(12) United States Patent
Seehra et al.

(10) Patent No.: US 8,722,615 B2
(45) Date of Patent: May 13, 2014

(54) COMPOSITIONS AND METHODS FOR INCREASING SERUM HALF-LIFE

(75) Inventors: Jasbir Seehra, Lexington, MA (US); John Knopf, Carlisle, MA (US); Ravindra Kumar, Acton, MA (US)

(73) Assignee: Acceleron Pharma, Inc., Cambridge, MA (US)

( * ) Notice: Subject to any disclaimer, the term of this patent is extended or adjusted under 35 U.S.C. 154(b) by 249 days.

(21) Appl. No.: 12/959,220

(22) Filed: Dec. 2, 2010

(65) Prior Publication Data

US 2011/0171218 A1 Jul. 14, 2011

Related U.S. Application Data

(60) Provisional application No. 61/266,095, filed on Dec. 2, 2009, provisional application No. 61/327,582, filed on Apr. 23, 2010.

(51) Int. Cl.
*A61K 38/00* (2006.01)

(52) U.S. Cl.
USPC ............................................ 514/1.1; 530/350

(58) Field of Classification Search
None
See application file for complete search history.

(56) References Cited

U.S. PATENT DOCUMENTS

| | | | |
|---|---|---|---|
| 5,395,760 A | 3/1995 | Smith et al. |
| 5,447,851 A | 9/1995 | Beutler et al. |
| 5,605,690 A | 2/1997 | Jacobs et al. |
| 5,610,279 A | 3/1997 | Brockhaus et al. |
| 5,633,145 A | 5/1997 | Feldmann et al. |
| 5,705,364 A | 1/1998 | Etcheverry et al. |
| 5,721,121 A | 2/1998 | Etcheverry et al. |
| 5,770,401 A | 6/1998 | Mullarkey |
| 5,808,029 A | 9/1998 | Brockhaus et al. |
| 5,834,266 A | 11/1998 | Crabtree et al. |
| 5,863,786 A | 1/1999 | Feldmann et al. |
| 5,925,548 A | 7/1999 | Beutler et al. |
| 5,945,397 A | 8/1999 | Smith et al. |
| 5,990,109 A | 11/1999 | Chen et al. |
| 6,027,921 A | 2/2000 | Heartlein et al. |
| 6,043,082 A | 3/2000 | Crabtree et al. |
| RE36,755 E | 6/2000 | Smith et al. |
| 6,201,105 B1 | 3/2001 | Smith et al. |
| 6,265,535 B1 | 7/2001 | Greene et al. |
| 6,270,766 B1 | 8/2001 | Feldman et al. |
| 6,306,820 B1 | 10/2001 | Bendele et al. |
| 6,399,773 B1 | 6/2002 | Liu et al. |
| 6,413,744 B1 | 7/2002 | Morris et al. |
| 6,419,919 B2 | 7/2002 | Mountz et al. |
| 6,433,158 B1 | 8/2002 | Pettit |
| 6,441,136 B1 | 8/2002 | Pettit |
| 6,451,986 B1 | 9/2002 | Pettit |
| 6,498,165 B1 | 12/2002 | Armstrong et al. |
| 6,541,610 B1 | 4/2003 | Smith |
| 6,548,644 B1 | 4/2003 | Pettit |
| 6,572,852 B2 | 6/2003 | Smith et al. |
| 6,610,750 B1 | 8/2003 | Charbit et al. |
| 6,649,589 B1 | 11/2003 | Olmarker et al. |
| 6,673,908 B1 | 1/2004 | Stanton, Jr. |
| 6,693,181 B2 * | 2/2004 | Ashkenazi et al. .......... 536/23.4 |
| 6,746,671 B2 | 6/2004 | Steidler et al. |
| 6,800,300 B1 | 10/2004 | Miller et al. |
| 6,846,828 B2 | 1/2005 | Hawley et al. |
| 6,861,441 B1 | 3/2005 | Clayton et al. |
| 6,872,549 B2 | 3/2005 | Van Ness et al. |
| 6,924,124 B1 | 8/2005 | Singh |
| 6,972,327 B1 | 12/2005 | Madani et al. |
| 6,974,681 B1 | 12/2005 | McGrew |
| 7,057,022 B2 | 6/2006 | Smith et al. |
| 7,067,279 B1 | 6/2006 | Follstad et al. |
| 7,070,783 B1 | 7/2006 | Chernajovsky et al. |
| 7,091,321 B2 | 8/2006 | Gillies et al. |
| 7,094,564 B1 | 8/2006 | Greene et al. |
| 7,122,641 B2 | 10/2006 | Vedantham et al. |
| 7,129,203 B2 | 10/2006 | Pettit |
| 7,138,371 B2 | 11/2006 | DeFrees et al. |
| 7,144,987 B1 | 12/2006 | Chirino et al. |
| 7,157,557 B2 | 1/2007 | Sassenfeld et al. |
| 7,175,847 B1 | 2/2007 | Anderson et al. |
| 7,229,962 B2 | 6/2007 | Chung et al. |
| 7,268,112 B2 | 9/2007 | Filvaroff et al. |
| 7,268,116 B2 | 9/2007 | Liang |
| 7,276,477 B2 | 10/2007 | Osslund et al. |
| 7,294,481 B1 | 11/2007 | Fung |
| 7,300,773 B2 | 11/2007 | Drapeau et al. |

(Continued)

FOREIGN PATENT DOCUMENTS

| | | | |
|---|---|---|---|
| EP | 1362062 B1 | 5/2005 |
| WO | WO-94/06476 A1 | 3/1994 |

(Continued)

OTHER PUBLICATIONS

Raju T. S. et al. Glycoengineering of Therapeutic Glycoproteins: In Vitro Galactosylation and Sialylation of Glycoproteins with Terminal N-Acetylglucosamine and Galactose Residues. Biochemistry 40(30): 8868-8876 (2001).
International Search Report for PCT/US2010/058765, dated Feb. 22, 2011.
Moreland et al., "Treatment of rheumatoid arthritis with a recombinant human tumor necrosis factor (p75)-Fc fusion protein," The New England Journal of Medicine, vol. 337(3), pp. 141-147 (1997).
International Search Report for PCT/US2012/041736 dated Sep. 25, 2012 (WO-063).
Mickle et al., "Genotype-phenotype relationships in cystic fibrosis," Medical Clinics of North America, 84(3):597-607 (2000).
Wells, J.A., "Additivity of Mutational Effects in Proteins," Biochemistry. 29(37):8509-8517 (1990).

(Continued)

*Primary Examiner* — Michael Pak
(74) *Attorney, Agent, or Firm* — Ropes & Gray LLP

(57) ABSTRACT

Provided herein are glycovariant Fc fusion proteins having increased serum half lives. Also provided are methods for increasing the serum half life of an Fc fusion protein by introducing one or more non-endogenous glycosylation sites.

24 Claims, 12 Drawing Sheets
(2 of 12 Drawing Sheet(s) Filed in Color)

(56) References Cited

U.S. PATENT DOCUMENTS

| | | |
|---|---|---|
| 7,384,765 B1 | 6/2008 | Follstad et al. |
| 7,416,858 B2 | 8/2008 | DeFrees et al. |
| 7,459,528 B2 | 12/2008 | Smith et al. |
| 7,476,722 B2 | 1/2009 | Vedantham et al. |
| 7,491,393 B2 | 2/2009 | Anderson et al. |
| 7,504,106 B2 | 3/2009 | Skurkovich et al. |
| 7,507,745 B2 | 3/2009 | Meade et al. |
| 7,510,712 B2 | 3/2009 | Anderson et al. |
| 7,541,328 B2 | 6/2009 | Hemberger et al. |
| 7,626,895 B2 | 12/2009 | Goodman et al. |
| 2002/0150582 A1 | 10/2002 | Friedrichs et al. |
| 2003/0148955 A1 | 8/2003 | Pluenneke |
| 2003/0180287 A1 | 9/2003 | Gombotz et al. |
| 2003/0195338 A1* | 10/2003 | Chung et al. .......... 530/351 |
| 2004/0220103 A1 | 11/2004 | Finck et al. |
| 2004/0235047 A1 | 11/2004 | Siber |
| 2005/0106148 A1 | 5/2005 | Kay et al. |
| 2007/0010661 A1 | 1/2007 | Vedantham et al. |
| 2007/0048837 A1 | 3/2007 | Pettit |
| 2007/0243185 A1 | 10/2007 | Gombotz et al. |
| 2008/0213215 A1 | 9/2008 | Krishnan et al. |
| 2008/0274507 A1 | 11/2008 | Gomes et al. |
| 2009/0270592 A1 | 10/2009 | Smith et al. |
| 2010/0068215 A1 | 3/2010 | Seehra et al. |
| 2010/0172868 A1 | 7/2010 | Morrison et al. |
| 2011/0171218 A1 | 7/2011 | Seehra et al. |

FOREIGN PATENT DOCUMENTS

| | | |
|---|---|---|
| WO | WO-96/34095 A1 | 10/1996 |
| WO | WO-99/11662 A1 | 3/1999 |
| WO | WO-99/11791 A2 | 3/1999 |
| WO | WO-99/41374 A2 | 8/1999 |
| WO | WO-99/43713 A1 | 9/1999 |
| WO | WO-00/50436 A1 | 8/2000 |
| WO | WO-00/60079 A2 | 10/2000 |
| WO | WO-01/38526 A1 | 5/2001 |
| WO | WO-01/85782 A2 | 11/2001 |
| WO | WO-02/20762 A2 | 3/2002 |
| WO | WO-03/072035 A2 | 9/2003 |
| WO | WO-2004/091499 A2 | 10/2004 |
| WO | WO-2004/113387 A2 | 12/2004 |
| WO | WO-2005/014035 A2 | 2/2005 |
| WO | WO-2005/077415 A1 | 8/2005 |
| WO | WO-2006/001023 A2 | 1/2006 |
| WO | WO-2006/007881 A2 | 1/2006 |
| WO | WO-2006/079176 A1 | 8/2006 |
| WO | WO-2006/083970 A2 | 8/2006 |
| WO | WO-2006/085938 A2 | 8/2006 |
| WO | WO-2007/041964 A1 | 4/2007 |
| WO | WO-2008/011633 A2 | 1/2008 |
| WO | WO-2008/025856 A2 | 3/2008 |
| WO | WO-2008/051306 A1 | 5/2008 |
| WO | WO-2008/135972 A2 | 11/2008 |
| WO | WO-2008/145139 A1 | 12/2008 |
| WO | WO-2008/151258 A2 | 12/2008 |
| WO | WO-2009/012600 A1 | 1/2009 |
| WO | WO-2009/089396 A2 | 7/2009 |
| WO | WO-2010/033854 A2 | 3/2010 |
| WO | WO-2010/144452 A1 | 12/2010 |
| WO | WO-2010/151426 A1 | 12/2010 |
| WO | WO-2011/068993 A1 | 6/2011 |
| WO | WO-2012/170938 | 12/2012 |

OTHER PUBLICATIONS

Jones et al., "Controlling N-linked glycan site occupancy," Biochemica et Biophysica Acta General Subjects, Elsevier Science Publishers, NL, 1726(2):121-137 (2005).

Sola et al., "Effects of glycosylation on the stability of protein pharmaceuticals," Journal of Pharmaceutical Sciences, 98(4):1223-1245, XP055057795, ISSN: 0022-3549, DOI: 10/2002/jps.21504,2008.

Werner et al., "Glycosylation of therapeutic proteins in different production systems," Acta Pediatrica, Universitetsforlaget, Oslo, NO. 96(455):17-22, XP008080645, ISSN: 0803-5253 (2007).

* cited by examiner

```
LPAQVAFTPY APEPGSTCRL REYYDQTAQM CCSKCSPGQH AKVFCTKTSD
TVCDSCEDST YTQLWNWVPE CLSCGSRCSS DQVETQACTR EQNRICTCRP
GWYCALSKQE GCRLCAPLRK CRPGFGVARP GTETSDVVCK PCAPGTFSNT
TSSTDICRPH QICNVVAIPG NASMDAVCTS TSPTRSMAPG AVHLPQPVST
RSQHTQPTPE PSTAPSTSFL LPMGPSPPAE GSTGDEPKSC DKTHTCPPCP
APELLGGPSV FLFPPKPKDT LMISRTPEVT CVVVDVSHED PEVKFNWYVD
GVEVHNAKTK PREEQYNSTY RVVSVLTVLH QDWLNGKEYK CKVSNKALPV
PIEKTISKAK GQPREPQVYT LPPSREEMTK NQVSLTCLVK GFYPSDIAVE
WESNGQPENN YKTTPPVLDS DGSFFLYSKL TVDKSRWQQG NVFSCSVMHE
ALHNHYTQKS LSLSPGK (SEQ ID NO: 5)
```

Figure 1

```
MAPVAVWAAL AVGLELWAAA HALPAQVAFT PYAPEPGSTC RLREYYDNTS
QMCCSKCSPG QHAKVFCTKT SDTVCDSCED STYTQLWNWV PECLSCGSRC
SSDQVETQAC TREQNRICTC RPGWYCALSK QEGCRLCAPL RKCRPGFGVA
RPGTETSDVV CKPCAPGTFS NTTSSTDICR PHQICNVVAI PGNASMDAVC
TSTSPTRSMA PGAVHLPQPV STRSQHTQPT PEPSTAPSTS FLLPMGPSPP
AEGSTGDEPK SCDKTHTCPP CPAPELLGGP SVFLFPPKPK DTLMISRTPE
VTCVVVDVSH EDPEVKFNWY VDGVEVHNAK TKPREEQYNS TYRVVSVLTV
LHQDWLNGKE YKCKVSNKAL PAPIEKTISK AKGQPREPQV YTLPPSREEM
TKNQVSLTCL VKGFYPSDIA VEWESNGQPE NNYKTTPPVL DSDGSFFLYS
KLTVDKSRWQ QGNVFSCSVM HEALHNHYTQ KSLSLSPGK  (SEQ ID NO:6)
```

Figure 2

```
MAPVAVWAAL AVGLELWAAA HALPAQVAFT PYAPEPGSTC RLREYYNQTA
QMCCSKCSPG QHAKVFCTKT SDTVCDSCED STYTQLWNWV PECLSCGSRC
SSDQVETQAC TREQNRICTC RPGWYCALSK QEGCRLCAPL RKCRPGFGVA
RPGTNTSDVV CKPCAPGTFS NTTSSTDICR PHQICNVVAI PGNASMDAVC
TSTSPTRSMA PGAVHLPQPV STRSQHTQPT PEPSTAPSTS FLLPMGPSPP
AEGSTGDEPK SCDKTHTCPP CPAPELLGGP SVFLFPPKPK DTLMISRTPE
VTCVVVDVSH EDPEVKFNWY VDGVEVHNAK TKPREEQYNS TYRVVSVLTV
LHQDWLNGKE YKCKVSNKAL PAPIEKTISK AKGQPREPQV YTLPPSREEM
TKNQVSLTCL VKGFYPSDIA VEWESNGQPE NNYKTTPPVL DSDGSFFLYS
KLTVDKSRWQ QGNVFSCSVM HEALHNHYTQ KSLSLSPGK  (SEQ ID NO: 7)
```

Figure 3

```
MAPVAVWAAL  AVGLELWAAA  HALPAQVAFT  PYAPEPGSTC  RLREYYNQTA
QMCCSKCSPG  QHAKVFCTKT  SDTVCDSCED  STYTQLWNWV  PECLSCGSRC
SSDQVETQAC  TREQNRICTC  RPGWYCALSK  QEGCRLCAPL  RKCRPGFGVA
RPGTETSDVV  CKPCAPGTFS  NTTSSTDICR  PHQICNVVAI  PGNASMDAVC
TSTSPTRSMA  PGAVHLPQPV  STRSQHTQPT  PEPSTAPSTS  FLLPMGPSPP
AENSTGDEPK  SCDKTHTCPP  CPAPELLGGP  SVFLFPPKPK  DTLMISRTPE
VTCVVVDVSH  EDPEVKFNWY  VDGVEVHNAK  TKPREEQYNS  TYRVVSVLTV
LHQDWLNGKE  YKCKVSNKAL  PAPIEKTISK  AKGQPREPQV  YTLPPSREEM
TKNQVSLTCL  VKGFYPSDIA  VEWESNGQPE  NNYKTTPPVL  DSDGSFFLYS
KLTVDKSRWQ  QGNVFSCSVM  HEALHNHYTQ  KSLSLSPGK*  (SEQ ID NO: 8)
```

Figure 4

```
ATGGCGCCC GTCGCCGTC TGGGCCGCG CTGGCCGTC GGACTGGAG CTCTGGGCT
GCGGCGCAC GCCTTGCCC GCCCAGGTG GCATTTACA CCCTACGCC CCGGAGCCC
GGGAGCACA TGCCGGCTC AGAGAATAC TATGACCAG ACAGCTCAG ATGTGCTGC
AGCAAATGC TCGCCGGGC CAACATGCA AAAGTCTTC TGTACCAAG ACCTCGGAC
ACCGTGTGT GACTCCTGT GAGGACAGC ACATACACC CAGCTCTGG AACTGGGTT
CCCGAGTGC TTGAGCTGT GGCTCCCGC TGTAGCTCT GACCAGGTG GAAACTCAA
GCCTGCACT CGGGAACAG AACCGCATC TGCACCTGC AGGCCCGGC TGGTACTGC
GCGCTGAGC AAGCAGGAG GGGTGCCGG CTGTGCGCG CCGCTGCGC AAGTGCCGC
CCGGGCTTC GGCGTGGCC AGACCAGGA ACTGAAACA TCAGACGTG GTGTGCAAG
CCCTGTGCC CCGGGGACG TTCTCCAAC ACGACTTCA TCCACGGAT ATTTGCAGG
CCCCACCAG ATCTGTAAC GTGGTGGCC ATCCCTGGG AATGCAAGC ATGGATGCA
GTCTGCACG TCCACGTCC CCCACCCGG AGTATGGCC CCAGGGGCA GTACACTTA
CCCCAGCCA GTGTCCACA CGATCCCAA CACACGCAG CCAACTCCA GAACCCAGC
ACTGCTCCA AGCACCTCC TTCCTGCTC CCAATGGGC CCCAGCCCC CCAGCTGAA
GGGAGCACT GGCGACGAG CCCAAATCT TGTGACAAA ACTCACACA TGCCCACCG
TGCCCAGCA CCTGAACTC CTGGGGGGA CCGTCAGTC TTCCTCTTC CCCCCAAAA
CCCAAGGAC ACCCTCATG ATCTCCCGG ACCCCTGAG GTCACATGC GTGGTGGTG
GACGTGAGC CACGAAGAC CCTGAGGTC AAGTTCAAC TGGTACGTG GACGGCGTG
GAGGTGCAT AATGCCAAG ACAAAGCCG CGGGAGGAG CAGTACAAC AGCACGTAC
CGTGTGGTC AGCGTCCTC ACCGTCCTG CACCAGGAC TGGCTGAAT GGCAAGGAG
TACAAGTGC AAGGTCTCC AACAAAGCC CTCCCAGCC CCCATCGAG AAAACCATC
TCCAAAGCC AAAGGGCAG CCCCGAGAA CCACAGGTG TACACCCTG CCCCCATCC
CGGGAGGAG ATGACCAAG AACCAGGTC AGCCTGACC TGCCTGGTC AAAGGCTTC
TATCCCAGC GACATCGCC GTGGAGTGG GAGAGCAAT GGGCAGCCG GAGAACAAC
TACAAGACC ACGCCTCCC GTGCTGGAC TCCGACGGC TCCTTCTTC CTCTATAGC
AAGCTCACC GTGGACAAG AGCAGGTGG CAGCAGGGG AACGTCTTC TCATGCTCC
GTGATGCAT GAGGCTCTG CACAACCAC TACACGCAG AAGAGCCTC TCCCTGTCC
CCGGGTAAA TGA (SEQ ID NO: 9)
```

Figure 5

```
                                                           D1
MAPVAVWAAL AVGLELWAAA HALPAQVAFT PYAPEPGSTC RLREYYDQTA
              D2
QMCCSKCSPG QHAKVFCTKT SDTVCDSCED STYTQLWNWV PECLSCGSRC
              D3
SSDQVETQAC TREQNRICTC RPGWYCALSK QEGCRLCAPL RKCRPGFGVA
    D4
RPGTETSDVV CKPCAPGTFS NTTSSTDICR PHQICNVVAI PGNASMDAVC
  D5                      D6
TSTSPTRSMA PGAVHLPQPV STRSQHTQPT PEPSTAPSTS FLLPMGPSPP
  D7
AEGSTGD

Region D1
WT   YYDQTAQM
Mut  YYDNTSQM (Q48N/A50S)
Mut  YYNQTAQM (D47N)

Region D2
WT   GQHAKVF
Mut  GQNATVF (H62N/K64T)

Region D3
WT   REQNRIC
Mut  RENNSIC (Q114N/R116S)

Region D4
WT   GTETSDV
Mut  GTNTSDV (E155N)

Region D5
WT   CTSTSPTR
Mut  CTNTSPTR (S202N)
Mut  CTSNSSTR (T203N/P205S)

Region D6
WT   VSTRSQH
Mut  VSNRSQH (T222N)

Region D7
WT   AEGSTGD
Mut  AENSTGD (G253N)
```

Figure 7

```
TNFR_ECD    23  LPAQVAFTPYAPEPGSTCELREYYDQTAQMCCSKCSPGQHAKVFCTKTSDTVCDSCEDSTY  83
Sec Struct TNFR_ECD    84  TQLWNWVPECLSCGSKCSSDQVETQACTREQHRICTCRPGWYCALSKQEGCRLCAPLRKCR  144
Sec Struct TNFR_ECD   145  PGFGVARPGTETSDVVCKPCAPGTFSNTTSSTDICRPHQICNVVAIPGNASMDAVCTSTSP  205
Sec Struct TNFR_ECD   206  IRSMAPGAVHLPQPVSTRSQHTQPTPEPSTAPSTSFLLPMGPSPPAEGSTGD           257
Sec Struct
```

Figure 8

```
  1  MAPVAVWAAL  AVGLELWAAA  HALPAQVAFT  PYAPEPGSTC  RLREYYDQTA
 51  QMCCSKCSPG  QHAKVFCTKT  SDTVCDSCED  STYTQLWNWV  PECLSCGSRC
101  SSDQVETQAC  TREQNRICTC  RPGWYCALSK  QEGCRLCAPL  RKCRPGFGVA
151  RPGTETSDVV  CKPCAPGTFS  NTTSSTDICR  PHQICNVVAI  PGNASMDAVC
201  TSTSPTRSMA  PGAVHLPQPV  STRSQHTQPT  PEPSTAPSTS  FLLPMGPSPP
251  AEGSTGDTGG  GTHTCPPCPA  PELLGGPSVF  LFPPKPKDTL  MISRTPEVTC
301  VVVDVSHEDP  EVKFNWYVDG  VEVHNAKTKP  REEQYNSTYR  VVSVLTVLHQ
351  DWLNGKEYKC  KVSNKALPAP  IEKTISKAKG  QPREPQVYTL  PPSREEMTKN
401  QVSLTCLVKG  FYPSDIAVEW  ESNGQPENNY  KTTPPVLDSD  GSFFLYSKLT
451  VDKSRWQQGN  VFSCSVMHEA  LHNHYTQKSL  SLSPGK  (SEQ ID NO: 16)
```

Figure 9

```
   1  ATGGCGCCCG TCGCCGTCTG GGCCGCGCTG GCCGTCGGAC TGGAGCTCTG GGCTGCGGCG
  61  CACGCCTTGC CCGCCCAGGT GGCATTTACA CCCTACGCCC CGGAGCCCGG GAGCACATGC
 121  CGGCTCAGAG AATACTATGA CCAGACAGCT CAGATGTGCT GCAGCAAATG CTCGCCGGGC
 181  CAACATGCAA AAGTCTTCTG TACCAAGACC TCGGACACCG TGTGTGACTC CTGTGAGGAC
 241  AGCACATACA CCCAGCTCTG GAACTGGGTT CCCGAGTGCT TGAGCTGTGG CTCCCGCTGT
 301  AGCTCTGACC AGGTGGAAAC TCAAGCCTGC ACTCGGGAAC AGAACCGCAT CTGCACCTGC
 361  AGGCCCGGCT GGTACTGCGC GCTGAGCAAG CAGGAGGGGT GCCGGCTGTG CGCGCCGCTG
 421  CGCAAGTGCC GCCCGGGCTT CGGCGTGGCC AGACCAGGAA CTGAAACATC AGACGTGGTG
 481  TGCAAGCCCT GTGCCCCGGG GACGTTCTCC AACACGACTT CATCCACGGA TATTTGCAGG
 541  CCCCACCAGA TCTGTAACGT GGTGGCCATC CCTGGGAATG CAAGCATGGA TGCAGTCTGC
 601  ACGTCCACGT CCCCCACCCG GAGTATGGCC CCAGGGGCAG TACACTTACC CCAGCCAGTG
 661  TCCACACGAT CCCAACACAC GCAGCCAACT CCAGAACCCA GCACTGCTCC AAGCACCTCC
 721  TTCCTGCTCC CAATGGGCCC CAGCCCCCCA GCTGAAGGGA GCACTGGCGA CACCGGTGGT
 781  GGAACTCACA CATGCCCACC GTGCCCAGCA CCTGAACTCC TGGGGGGACC GTCAGTCTTC
 841  CTCTTCCCCC CAAAACCCAA GGACACCCTC ATGATCTCCC GGACCCCTGA GGTCACATGC
 901  GTGGTGGTGG ACGTGAGCCA CGAAGACCCT GAGGTCAAGT TCAACTGGTA CGTGGACGGC
 961  GTGGAGGTGC ATAATGCCAA GACAAAGCCG CGGGAGGAGC AGTACAACAG CACGTACCGT
1021  GTGGTCAGCG TCCTCACCGT CCTGCACCAG GACTGGCTGA ATGGCAAGGA GTACAAGTGC
1081  AAGGTCTCCA ACAAAGCCCT CCCAGCCCCC ATCGAGAAAA CCATCTCCAA AGCCAAAGGG
1141  CAGCCCCGAG AACCACAGGT GTACACCCTG CCCCCATCCC GGGAGGAGAT GACCAAGAAC
1201  CAGGTCAGCC TGACCTGCCT GGTCAAAGGC TTCTATCCCA GCGACATCGC CGTGGAGTGG
1261  GAGAGCAATG GGCAGCCGGA GAACAACTAC AAGACCACGC CTCCCGTGCT GGACTCCGAC
1321  GGCTCCTTCT TCCTCTATAG CAAGCTCACC GTGGACAAGA GCAGGTGGCA GCAGGGGAAC
1381  GTCTTCTCAT GCTCCGTGAT GCATGAGGCT CTGCACAACC ACTACACGCA GAAGAGCCTC
1441  TCCCTGTCTC CGGGTAAATG A (SEQ ID NO: 17)
```

Figure 10

COMPOSITIONS AND METHODS FOR INCREASING SERUM HALF-LIFE

RELATED APPLICATIONS

This application claims the benefit of U.S. Provisional Application Nos. 61/266,095, filed on Dec. 2, 2009 and 61/327,582, filed on Apr. 23, 2010. All the teachings of the above-referenced applications are incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 21, 2011,l is named PHPH0261.txt and is 49,591 bytes in size.

BACKGROUND

Therapeutic proteins or peptides in their native state, or when recombinantly produced, are typically labile molecules exhibiting short periods of stability or short serum half-lives. In addition, these molecules are often extremely labile when formulated, particularly when formulated in aqueous solutions for diagnostic and therapeutic purposes. Few practical solutions exist to extend or promote the stability in vivo or in vitro of proteinaceous therapeutic molecules. Many therapeutics, in particular peptide drugs, suffer from inadequate serum half-lives in vivo. This necessitates the administration of such therapeutics at high frequencies and/or higher doses, or the use of sustained release formulations, in order to maintain the serum levels necessary for therapeutic effects. Frequent systemic administration of drugs is associated with considerable negative side effects. For example, frequent, e.g. daily, systemic injections represent a considerable discomfort to the subject, pose a high risk of administration related infections, and may require hospitalization or frequent visits to the hospital, in particular when the therapeutic is to be administered intravenously. Moreover, in long-term treatments daily intravenous injections can also lead to considerable tissue scarring and vascular pathologies caused by the repeated puncturing of vessels. Similar problems are known for all frequent systemic administrations of therapeutics, for example, the administration of insulin to diabetics, or interferon drugs in patients suffering from multiple sclerosis. All these factors lead to a decreased patient compliance and increased costs for the health system.

One possible solution to modify serum half-life of a pharmaceutical agent is to covalently attach to the agent molecules that may increase the half-life. Previously, it has been shown that attachment of polymers, such as polyethylene glycol or "PEG", to polypeptides may increase their serum half-lives. However, the attachment of polymers can lead to decreases in drug activity. Incomplete or non-uniform attachment leads to a mixed population of compounds having differing properties. Additionally, the changes in half-lives resulting from such modifications are unpredictable. For example, conjugation of different polyethylene glycols to IL-8, G-CSF and IL-1ra produced molecules having a variety of activities and half-lives (Gaertner and Offord, (1996), Bioconjugate Chem. 7:38-44). Conjugation of IL-8 to $PEG_{20}$ produced no change in its half-life, while conjugation of $PEG_{20}$ to IL-1ra gave an almost seven-fold increase in half-life. Additionally, the IL-8/$PEG_{20}$ conjugate was ten- to twenty-fold less effective than the native protein.

Accordingly, methods that are capable of increasing the serum half-life of a biologically active molecule, without seriously diminishing the biological function of the molecule, would be highly desirable.

SUMMARY

In part, the disclosure provides methods for extending the serum half-life of a fusion protein comprising an immunoglobulin Fc domain and at least one heterologous polypeptide domain. In certain embodiments, the methods include preparing a modified nucleic acid encoding a modified Fc fusion protein that has an extended serum half-life relative to an initial Fc fusion protein by modifying the nucleic acid encoding the heterologous portion of the initial Fc fusion protein to code for one or more additional N-linked glycosylation sites. In some embodiments, the modified nucleic acid of the invention will encode a modified Fc fusion protein that, when expressed in a suitable cell culture, has a serum half-life at least 10% longer than the serum half-life of the initial Fc fusion protein. In some embodiments, the modified Fc fusion protein of the invention has substantially the same or greater in vivo biological activity relative to the unmodified Fc fusion protein. In certain embodiments, glycosylation at one or more of the additional (i.e., introduced) glycosylation sites increases the half-life (e.g., in vitro, in vivo, serum half-life) of the modified Fc fusion protein by at least 10%, 20%, 30%, 40%, 50%, 75%, 100%, 125%, 150%, 175%, 200%, 225%, or 250% or more relative to the serum half-life of a fusion polypeptide lacking the additional glycosylation site. In certain embodiments, serum half-life of a modified Fc fusion protein and a fusion polypeptide lacking the additional glycosylation site are measured in the same animal model or species for comparison. In exemplary embodiments, the serum half-life is measured in a pharmacokinetic rat assay or a pharmacokinetic monkey assay as described herein.

In some embodiments, the disclosure provides a method for preparing a modified Fc fusion protein that has an extended half-life relative to an initial Fc fusion protein by a) expressing a nucleic acid that has been modified to introduce at least one additional N-linked glycosylation site in a cell culture that provides mammalian or mammalian-like glycosylation, and b) recovering the modified Fc fusion protein from the cell culture. Fc fusion proteins may be recovered as crude, partially purified, or highly purified fractions using any technique suitable for obtaining protein from cell cultures. In certain aspects the modified nucleic acid is expressed in a cell line that generates N-linked sugar moieties that comprise sialic acid. In certain aspects, the modified nucleic acid is expressed by a mammalian cell line, including but not limited to, a CHO cell line, a NSO cell line, a COS cell line, or a HEK236 cell line. In other aspects, the modified nucleic acid is expressed by a non-mammalian cell that has been engineered to provide mammalian or mammalian-like glycosylation, including but not limited to, genetically engineered fungal cells, insect cells, or plant cells. In certain aspects, purification may include the steps of exposing modified Fc fusion protein to protein A and recovering the modified Fc fusion protein that is bound to the protein A. In preferred embodiments, the Fc fusion proteins produced by the methods of the disclosure are formulated for administration to a patient.

In some embodiments, the disclosure provides a cell line comprising a modified nucleic acid prepared to according any of the methods described herein. A cell line of the invention may include a mammalian cell line (e.g., CHO cell line, a NSO cell line, a COS cell line, or a HEK236 cell line) or a non-mammalian cell line (e.g., fungal cells, insect cells, or plant cells), which has been genetically modified to provide mammalian or mammalian-like glycosylation.

In certain embodiments, the disclosure provides glycovariant Fc fusion proteins characterized by increased stability and/or serum half life and methods for producing fusion proteins having increased half-lives. Fc-fusion proteins of the invention include, but are not limited to, polypeptides comprising an immunoglobulin Fc domain and at least one heterologous polypeptide domain. The Fc-fusion proteins are modified outside of the immunoglobulin Fc domain to introduce at least one non-endogenous N-linked glycosylation site, which increases the serum half-life of the modified fusion protein relative to the half-life (e.g., in vitro, in vivo, or serum half-life) of the fusion protein lacking the introduced glycosylation site. In certain embodiments, a fusion protein of the invention comprise at least one non-endogenous, or introduced, N-linked glycosylation site that increases the serum half-life of the fusion by at least 10%, 20%, 30%, 40%, 50%, 75%, 100%, 125%, 150%, 175%, 200%, 225%, or 250% or more relative to the serum half-live of a fusion protein lacking the introduced glycosylation site. In certain embodiments, serum half-life of a modified Fc fusion protein and a fusion polypeptide lacking the additional glycosylation site are measured in the same animal model or species for comparison. In exemplary embodiments, the serum half-life is measured in a pharmacokinetic rat assay or a pharmacokinetic monkey assay as described herein.

Fc fusion proteins of the invention may be modified by the addition, deletion, or substitution of one or more amino acid residues to introduce one N-linked glycosylation site. In certain embodiments, the heterologous portion of the initial Fc fusion protein comprises at least one N-linked glycosylation site per each 50, 55, 60, 65, 70, 75, 80, 85, 90, 95 100, 105 110, 115, 120, 130, 140, or 150 amino acids. In certain embodiments, the heterologous portion of the initial Fc fusion protein comprises fewer than one N-linked glycosylation site per each 60, 70, 80, 90, 100, 110, 120, or 125 amino acids. In certain embodiments, each amino acid of the heterologous portion of the modified Fc fusion protein that is attached to an N-linked glycosylation is separated by at least 15, 20, 30, 40, 50, 60, 70, 80, 90, or 100 amino acids from any other amino acid modified by an N-linked glycosylation. In certain embodiments, the additional N-linked glycosylation site does not occur within 10, 20, 30, 40, or 50 amino acids of the N-terminus, C-terminus, or both N- and C-termini of the modified Fc fusion protein.

In preferred embodiments, Fc fusion proteins of the invention comprises at least two structurally distinct domains that are connected by an amino acid sequence that is surface exposed (i.e., a soluble loop domain) and not incorporated into an α-helix or β-sheet. In preferred embodiments, additional N-linked glycosylation sites are positioned within amino acid sequences that are surface exposed. In preferred embodiments, additional N-linked glycosylation sites are not incorporated into a region of the protein having a secondary structural element, e.g., an α-helix or β-sheet. Heterologous portions of use in the instant invention may include a functional domain of a protein (e.g., an enzymatic or catalytic domain or ligand binding domain). In some embodiments, the Fc fusion protein of the disclosure further comprises a linker domain. In some embodiments, at least one of the introduced glycosylation sites is located in the linker domain. A heterologous domain of a fusion polypeptide of the invention is preferably of higher molecular weight, being at least 25, 30, 35, 40, 45, 50, 55, 60, 65, 70, 75, 80, 85, 90, 95, 100, 105, or 110 kDa.

In specific embodiments, the heterologous portion comprises an extracellular (i.e., soluble) domain of a cellular receptor (e.g., transmembrane receptor) as well as any variants thereof (including mutants, fragments, and peptidomimetic forms). In preferred embodiments, the heterologous potion includes a ligand binding domain of a transmembrane receptor. Methods of the disclosure may be used to introduce one or more N-linked glycosylation sites at positions of the heterologous such that any additional sugar moieties attached do not substantially interfere with the ligand binding domain, e.g., less than a 2-, 3-, 5-, 10-, or 15-fold reduction in binding activity relative to ligand binding to the Fc-fusion protein lacking the introduced glycosylation site. Therefore, in some aspects, one or more of the introduced N-linked glycosylation sites are introduced at positions such that the amino acid sequence of the ligand binding domain is not modified and/or at positions that are predicted not to interfere substantially with the ligand interface. In certain embodiments, the Fc fusion protein has an $IC_{50}$ (i.e., half maximal inhibitory concentration) that is no more than two-, three-, five- or ten-fold less than that of the initial Fc fusion protein.

In certain embodiments, the Fc-fusion protein comprises a heterologous portion selected from a member of the nerve growth factor/tumor necrosis factor receptor family. In specific embodiments, the extracellular receptor domain comprises a portion of the tumor necrosis factor type 2 receptor (i.e., TNFR2). In preferred embodiments, the disclosure provides TNFR2 fusion proteins that bind to TNF-α with a $K_D$ less than 1 micromolar or less than 100, 10 or 1 nanomolar. In some embodiments, TNFR2 fusion proteins of invention comprise a TNFR2 extracellular domain having one or more modified amino acids located at positions D47, Q48, A50, E155, or G253 of the human TNFR2 precursor protein (i.e., SEQ ID NO: 1). These residues correspond to positions D25, Q26, A28, E133, and G231, respectively, of the extracellular, processed domain of TNFR2 (i.e., SEQ ID NO: 2). Preferred modification include addition, substitution, and/or deletion of amino acids that result in the introduction of one or more N-linked glycosylation sites in a TNFR2 polypeptide including, for example, amino acid substitutions Q26N, A28S, D25N, E133N, D25N, G231N relative to the amino acid sequence of SEQ ID NO: 2. In some embodiments, more than one modification (e.g., additions, deletions, and/or substitutions) are made to a TNFR2 fusion protein to introduce one or more N-linked glycosylation sites including, for example, a TNFR2 variant comprising Q26N/A28S; D25N/E133N; D25N/G231N; Q26N/A28S/E133N; Q26N/A28S/G231N; or E133N/G231N substitutions relative to the amino acid sequence of SEQ ID NO: 2. A TNFR2-Fc fusion protein of the invention may be any of those disclosed herein, such as a fusion protein comprising a polypeptide having an amino acid sequence selected from SEQ ID NOs: 1, 2, 5, 6, 7, or 8 or comprising an amino acid sequence that is at least 80%, 85%, 90%, 95%, 97% or 99% identical to an amino acid sequence selected from SEQ ID NOs: 1, 2, 5, 6, 7 or 8. TNFR2-Fc fusion proteins may be formulated as a pharmaceutical preparation comprising the TNFR2-Fc fusion protein and a pharmaceutically acceptable carrier, wherein the preparation is substantially free of pyrogenic materials so as to be suitable for administration of a mammal. The composition may be at least 95% pure, with respect to other polypeptide components, as assessed by size exclusion chromatography, and optionally, the composition is at least 98% pure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows the amino acid sequence of a TNFR2-h(1)Fc polypeptide (SEQ ID NO: 5). A soluble TNFR2 fusion protein is depicted having the extracellular domain of human TNFR2 fused without linker to an immunoglobulin Fc domain, designated the h(1)Fc variant. The immunoglobulin Fc region is underlined once and the naturally occurring N-linked glycosylation sites are double underlined.

FIG. 2 shows the amino acid sequence of a Q48N/A50S variant TNFR2-h(1)Fc polypeptide (SEQ ID NO: 6). A soluble TNFR2 fusion protein is depicted having the extracellular domain of human TNFR2 fused without linker to an h(1)Fc immunoglobulin Fc domain. The naturally occurring TNFR2-Fc extracellular domain was modified at positions 48 and 50 to introduce an N-linked glycosylation site. The immunoglobulin Fc region is underlined once and the substituted amino acids are double underlined.

FIG. 3 shows the amino acid sequence of a variant (D47N/E155N) TNFR2-h(1)Fc polypeptide (SEQ ID NO: 7). A soluble TNFR2 fusion protein is depicted having the extracellular domain of human TNFR2 fused without linker to an h(1)Fc immunoglobulin Fc domain. The naturally occurring TNFR2-Fc extracellular domain was modified at positions 47 and 155 to introduce an N-linked glycosylation site. The immunoglobulin Fc region is underlined once and the substituted amino acids are double underlined.

FIG. 4 shows the amino acid sequence of a variant (D47N/G253N) TNFR2-h(1)Fc polypeptide (SEQ ID NO: 8). A soluble TNFR2 fusion protein is depicted having the extracellular domain of human TNFR2 fused without linker to an h(1)Fc immunoglobulin Fc domain. The naturally occurring TNFR2-Fc extracellular domain was modified at positions 47 and 253 to introduce an N-linked glycosylation site. The immunoglobulin Fc region is underlined once and the substituted amino acids double underlined.

FIG. 5 shows the nucleic acid sequence encoding the TNFR2-h(1)Fc polypeptide (i.e., SEQ ID NO:5) with a natural leader sequence (SEQ ID NO: 9).

FIG. 7 shows the sequence of the extracellular domain of TNFR2 (SEQ ID NO: 26) with exemplary amino acid modification for introducing non-endogenous glycosylation sites being highlighted. Specific examples of modifications that would introduce a non-endogenous glycosylation site are indicated for each highlighted region (SEQ ID NO: 27-42, respectively, in order of appearance). The signal peptide is indicated with a single underline, and endogenous glycosylation sites are indicated with a double underline.

FIG. 8 shows the predicted location of beta strands (arrows) in the TNFR2 structure(SEQ ID NO: 43). Numbering is based on the native TNFR2 precursor sequence (SEQ ID NO: 1). Secondary structure was inferred by sequence comparison and structural homology with TNFR1 (PDB ID: 1EXT), cytokine response modifier E (CrmE; PDB ID: 2UWI), and CD134 (OX40; PDB ID: 2HEY).

FIG. 9 shows the amino acid sequence of a variant TNFR2-h(2)Fc polypeptide (SEQ ID NO: 16) with a native leader sequence. A soluble TNFR2 fusion protein is depicted having the extracellular domain of native human TNFR2 fused via a four-amino-acid linker to an exemplary human Fc domain (SEQ ID NO: 14). The Fc domain is indicated with a single underline, and the leader and linker sequences are double underlined.

FIG. 10 shows a nucleotide sequence (SEQ ID NO: 17) encoding the TNFR2-h(2)Fc polypeptide (i.e., SEQ ID NO: 16). The sequence encoding the Fc domain is indicated with a single underline, and sequences encoding the leader and linker are double underlined.

DETAILED DESCRIPTION

1. Overview

Figure 6:
FIG. 6 is a ribbon diagram depicting the binding interface between TNF and the extracellular domain of the TNFR2 receptor. TNF is the green ribbon structure on the left, while the TNFR2 receptor is blue ribbon structure on the right. Engineered sites to introduce N-linked glycosylation sites are shown in circles. Single mutations are represented by blue circles and double mutations are represented by green circles. Mutations that significantly reduced ligand binding activity are located proximal to the TNF binding site and are depicted as red circles.

In certain aspects, the present disclosure relates to the surprising discovery that the serum half-life of an Fc-fusion protein can be extended by the introduction of at least one non-endogenous N-linked glycosylation site at an appropriate position in an appropriate target protein. Accordingly, the disclosure provides methods for increasing the serum half-lives of Fc-fusions proteins, particular therapeutic polypeptides, by increasing the number of N-linked glycosylation sites on the polypeptide. As demonstrated herein, the methods of the disclosure have been used to increase the serum half-lives of Fc-fusion proteins comprising a portion of an extracellular domain of a receptor that includes a ligand binding domain. In specific examples, the disclosure provides modified TNFR2-Fc fusion proteins that are characterized by an increased half-life relative to the unmodified forms of the respective fusion proteins. While not restricting the disclosure to any particular mechanism of effect, it is proposed that the non-Fc portion of an Fc fusion protein (the "heterologous portion") is exposed to a variety of intracellular and extracellular environments during its residence time in a patient's body. These differing conditions may cause portions of the heterologous portion to become vulnerable as substrates for proteases or other enzymes or molecules that begin the process of protein modification or degradation. Thus, the disclosure provides a novel proposal that serum half-life of Fc fusion proteins is significantly affected by agents acting to degrade the heterologous portion, and that modifications that tend to protect the heterologous portion from such agents will lead to a greater serum half-life. As described herein, the addition of one or more N-linked glycosylation sites provides a single-step, biocompatible system for shielding vulnerable portions of heterologous domains from unwanted degradation or alteration and, in some instances, stabilizing desirable structural conformations of such molecules.

It can be difficult to predict a priori which positions in a heterologous domain of an initial Fc fusion protein are most amenable to an additional N-linked glycosylation site, and in the absence of any constraints or guidelines any one heterologous domain could theoretically be modified with a nearly limitless combination of one or more additional N-linked sites. Through work with different initial Fc fusion proteins, the applicants have found a variety of guidelines that allow one to modify an initial Fc fusion protein at a reasonable number of sites so as to arrive at a modified Fc fusion protein that exhibits an extended serum half-life relative to the initial Fc fusion protein while preserving biological activity (particularly in vivo biological activity) of the modified molecule. While not wishing to limit the scope of the overall disclosure, applicants have found that use of one or more of the following principles provides a feasible approach to generating an active, extended half-life Fc fusion protein: (1) N-linked glycosylation sites may be advantageously placed at surface exposed positions of the heterologous portion of an Fc fusion protein, whether determined by protein structure analysis or empirical method, and particularly at positions that are not contained within defined protein structure elements, such as alpha-helices or beta-sheets; (2) N-linked glycosylation sites may be advantageously placed at positions in the heterologous portion of an Fc fusion protein that, if subject to modification or degradation would cause substantial perturbation of protein structure or function (for example, many proteins have an unstructured region at the N-terminus that, if cleaved, causes little or no perturbation of the overall protein and its activity, and accordingly, an N-linked glycosylation site placed at such a position may have modest effect on serum half-life, while by contrast surface exposed regions located between structure elements exhibit a combination of high exposure and significant consequences to the protein if subject to undesirable degradation and therefore surface exposed amino acids between structure elements represent a desirable position for the introduction of an N-linked glycosylation site); (3) N-linked glycosylation sites may be placed at positions that do not interfere with a key functional site of the initial Fc fusion protein (e.g., a ligand binding surface or catalytic site), which may be achieved by selecting positions external to the functional site itself and/or selecting positions where any new N-linked sugar moiety would not protrude into the functional site; (4) the degree of effect to be achieved by the addition of an N-linked glycosylation site may be inversely proportional to the density of N-linked sugars already present in the initial Fc fusion protein, and therefore, the approach may be most effective with initial Fc fusion proteins that have a heterologous portion with a relatively low level of glycosylation (e.g., less than 1 N-linked site per 60, 70, 80, 90, 100, 110, 125 or more amino acids of the heterologous portion); (5) in both heavily and lightly glycosylated heterologous portions, the degree of effect to be achieved may be proportional to the spacing between N-linked glycosylation sites, meaning that one or more additional N-linked glycosylation sites may be advantageously placed at a relatively regular and distant spacing (e.g., greater than 10, 15, 20, 25, 30, 35 or 40 amino acids between the N residues of N-linked glycosylation sites) from existing N-linked glycosylation or other additional N-linked glycosylation sites—even in a heavily glycosylated protein, if the sugars are closely clustered, the addition of well-spaced N-linked sites may promote a significant increase in serum half-life. While the use of one or more of the above principles may permit one to design a single modified Fc fusion protein that exhibits an extended serum half life relative to the initial Fc fusion protein, it will often be beneficial to generate a plurality of modified Fc fusion proteins based on a single initial Fc fusion protein, test these altered forms and then test combinations of those modified forms that exhibit the best combination of increased half-life and retained biological activity.

In certain aspects, the present disclosure relates to methods for increasing the serum half-lives of Fc-fusions proteins, particular therapeutic polypeptides, by increasing the number of N-linked glycosylation sites on the polypeptide. As demonstrated herein, the methods of the disclosure have been used to increase the serum half-lives of Fc-fusion proteins comprising a portion of an extracellular domain of a receptor that includes a ligand binding domain. In specific examples, the disclosure provides modified TNFR2-Fc fusion proteins that are characterized by an increased half-life relative to the unmodified forms of the respective fusion proteins. Regardless of the mechanism, it is apparent from the data presented herein that introduction of additional glycosylation sites is an effective method of prolonging the half-life of high molecular weight biopharmaceuticals, in particular Fc-fusion proteins.

In specific embodiments, the disclosure provides modified TNFR2-Fc glycovariant fusion proteins characterized by increased serum half-life. Tumor Necrosis Factor (TNF) is a naturally occurring cytokine that is involved in normal inflammatory and immune responses. Tumor necrosis factor-α (TNFα) and tumor necrosis factor-β (TNFβ) are homologous multifunctional cytokines. The great similarities in structural and functional characteristics of these polypeptides have resulted in their collective description as tumor necrosis factor or "TNF." Activities generally ascribed to TNF include: release of other cytokines including IL-1, IL-6, GM-CSF, and IL-10, induction of chemokines, increase in adhesion molecules, growth of blood vessels, release of tissue destructive enzymes and activation of T cells. See, for example, Feldmann et al., 1997, Adv. Immunol., 64:283-350, Nawroth et al., 1986, J. Exp. Med., 163:1363-1375; Moser et al., 1989, J. Clin. Invest, 83:444-455; Shingu et al., 1993, Clin. Exp. Immunol. 94:145-149; MacNaul et al., 1992, Matrix Suppl., 1:198-199; and Ahmadzadeh et al., 1990, Clin. Exp. Rheumatol. 8:387-391. All of these activities can serve to enhance an inflammatory response.

TNF causes pro-inflammatory actions which result in tissue injury, such as inducing procoagulant activity on vascular endothelial cells (Pober, et al., J. Immunol. 136:1680 (1986)), increasing the adherence of neutrophils and lymphocytes (Pober, et al., J. Immunol. 138:3319 (1987)), and stimulating the release of platelet activating factor from macrophages, neutrophils and vascular endothelial cells (Camussi, et al., J. Exp. Med. 166:1390 (1987)). TNF is also associated with infections (Cerami, et al., Immunol. Today 9:28 (1988)), immune disorders, neoplastic pathologies (Oliff, et al., Cell 50:555 (1987)), autoimmune pathologies and graft-versus host pathologies (Piguet, et al., J. Exp. Med. 166:1280 (1987)). Among such TNF-associated disorders are congestive heart failure, inflammatory bowel diseases (including Crohn's disease), arthritis, and asthma.

In particular, TNF plays a central role in gram-negative sepsis and endotoxic shock (Michie, et al., Br. J. Surg. 76:670-671 (1989); Debets, et al., Second Vienna Shock Forum, p. 463-466 (1989); Simpson, et al., Crit. Care Clin. 5:27-47 (1989); Waage, et al., Lancet 1:355-357 (1987); Hammerle, et al., Second Vienna Shock Forum p. 715-718 (1989); Debets, et al., Crit. Care Med. 17:489-497 (1989); Calandra, et al., J. Infect. Dis. 161:982-987 (1990); Revhaug, et al., Arch. Surg. 123:162-170 (1988)), including fever, malaise, anorexia, and cachexia.

TNF initiates its biological effect through its interaction with specific, cell surface receptors on TNF-responsive cells. There are two distinct forms of the cell surface tumor necrosis factor receptor (TNFR), designated p75 (or Type 2) and p55

(or Type 1) (Smith et al., 1990, Science 248:1019-1023; Loetscher et al., 1990, Cell 61:351-359). TNFR Type 1 and TNFR Type 2 each bind to both TNFα and TNFβ. Biological activity of TNF is dependent upon binding to either cell surface TNFR. The Type 1 receptor (also termed TNF-R55, TNF-RI, or TNFR-β) is a 55 kd glycoprotein shown to transduce signals resulting in cytotoxic, anti-viral, and proliferative activities of TNF-α. The p75 receptor (also termed TNF-R75, TNFR2, or TNFR-α) is a 75 kDa glycoprotein that has also been shown to transduce cytotoxic and proliferative signals as well as signals resulting in the secretion of GM-CSF.

TNF antagonists, such as soluble TNFRs and anti-TNF antibodies, have been demonstrated to block TNF activity, causing a decrease in IL-1, GM-CSF, IL-6, IL-8, adhesion molecules and tissue destruction in response to TNF (Feldmann et al., 1997). The effect of TNF antagonism utilizing a hamster anti-mouse TNF antibody was tested in a model of collagen type II arthritis in DBA/1 mice (Williams et al., 1992, Proc. Natl. Acad. Sci. USA, 89:9784-9788). Treatment initiated after the onset of disease resulted in improvement in footpad swelling, clinical score, and histopathology of joint destruction. Other studies have obtained similar results using either antibodies (Thorbecke et al., 1992, Proc. Natl. Acad. Sci. USA, 89:7375-7379) or TNFR constructs (Husby et al., 1988, J. Autoimmun. 1:363-71; Tetta et al., 1990, Ann. Rheum. Dis. 49:665-667; Wooley et al., 1993, J. Immunol. 151:6602-6607; Piguet et al., 1992, Immunology 77:510-514).

Three specific TNF antagonists are currently FDA-approved: etanercept (Enbrel®), infliximab (Remicade®) and adalimumab (Humira®). One or more of these drugs is approved for the treatment of rheumatoid arthritis, juvenile rheumatoid arthritis, psoriasis, psoriatic arthritis, ankylosing spondylitis, and inflammatory bowel disease (Crohn's disease or ulcerative colitis).

Clinical trials of a recombinant version of the soluble human TNFR (p75) linked to the Fc portion of human IgG1 (sTNFR(p75):Fc, Enbrel®, Immunex) have shown that its administration resulted in significant and rapid reductions in RA disease activity (Moreland et al., 1997, N. Eng. J. Med., 337:141-147). In addition, safety data from a pediatric clinical trial for Enbrel® indicates that this drug is generally well-tolerated by patients with juvenile rheumatoid arthritis (JRA) (Garrison et al, 1998, Am. College of Rheumatology meeting, Nov. 9, 1998, abstract 584).

As noted above, Enbrel® is a dimeric fusion protein consisting of the extracellular ligand-binding portion of the human 75 kilodalton (p'75) TNFR linked to the Fc portion of human IgG1. The Fc component of Enbrel® contains the CH2 domain, the CH3 domain and hinge region, but not the CH1 domain of IgG1. Enbrel® is produced in a Chinese hamster ovary (CHO) mammalian cell expression system. It consists of 934 amino acids and has an apparent molecular weight of approximately 150 kilodaltons (Smith et al., 1990, Science 248:1019-1023; Mohler et al., 1993, J. Immunol. 151:1548-1561; U.S. Pat. No. 5,395,760 (Immunex Corporation, Seattle, Wash.); U.S. Pat. No. 5,605,690 (Immunex Corporation, Seattle, Wash.).

Enbrel® is currently indicated for reduction in signs and symptoms of moderately to severely active rheumatoid arthritis in patients who have had an inadequate response to one or more disease-modifying antirheumatic drugs (DMARDs). Enbrel® can be used in combination with methotrexate in patients who do not respond adequately to methotrexate alone. Enbrel® is also indicated for reduction in signs and symptoms of moderately to severely active polyarticular-course juvenile rheumatoid arthritis in patients who have had an inadequate response to one or more DMARDs (May 28, 1999). Enbrel® is given to RA patients at 25 mg twice weekly as a subcutaneous injection.

Currently, treatments using ENBREL preparations are administered subcutaneously twice weekly, which is costly, unpleasant and inconvenient for the patient. Accordingly, the present disclosure provides TNF antagonists comprising a soluble (e.g., extracellular) portion of an TNF binding receptor (e.g., Enbrel®) that has been modified to introduce at least one non-endogenous N-linked glycosylation site to increase the serum half-life of the modified polypeptide relative to the serum half-life of the soluble TNF receptor lacking the introduced glycosylation site.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

The term "pharmacokinetic properties" refers to the absorption, distribution, metabolism and excretion of a bioactive agent (e.g., small molecule, polypeptide drug, etc.).

2. Glycovariant Fc Fusion Proteins

Provided herein are glycovariant fusion proteins having an Fc domain from an immunoglobulin molecule linked to a heterologous polypeptide. The glycovariant fusion proteins contain at least one non-endogenous N-linked glycosylation site outside of the Fc domain of the fusion protein. The Fc domain may be linked either directly, or indirectly via a polypeptide linker, to the heterologous polypeptide. A non-endogenous glycosylation site may be introduced into the heterologous polypeptide, the linker, or both.

A "non-endogenous", "introduced", or "novel" glycosylation site refers to a glycosylation site that is not present in an unmodified version of the polypeptide. Accordingly, the glycovariant fusion proteins described herein have at least one additional N-linked glycosylation site as compared to the number of glycosylation sites present in the unmodified version of the fusion protein. For example, if the unmodified version of the fusion protein has two glycosylation sites outside of the Fc domain and one N-linked glycosylation site is introduced into the heterologous polypeptide, then the glycovariant fusion protein will have three N-linked glycosylation sites including two native glycosylation sites and one introduced glycosylation site. It should be understood that modification of a fusion protein to increase the number of glycosylation sites is not limited to a particular "wild-type" amino acid sequence because naturally occurring or man-made variants can also be modified according to the methods of this invention to increase the number of glycosylation sites.

It is well known that some proteins can support a large number of sugar side chains. The distance between O-linked glycosylation sites can be as few as every other amino acid (see, e.g., Kolset & Tveit (2008) Cell. Mol. Life Sci 65: 1073-1085 and Kiani et al. (2002) Cell Research 12(1): 19-32). For N-linked glycosylation sites, the distance between sites can be as few as three, four, five or six amino acids (see, e.g., Lundin et al. (2007) FEBS Letters 581:5601-5604 (2007); Apweiler et al. (1991) Biochimica et Biophysica Acta 1473:4-8, the entire contents of each of which are incorporated by reference herein). Accordingly, in certain embodiments at least about 1, 2, 3, 4, 5, 6, 7, 8, 9, 10, 15, 20, 25, 30, 35, 40, 45, 50, 55, 60, 65, 70, 75, 80, 85, 90, 95, or 100 or more N-linked glycosylation sites can be added to a fusion protein described herein. In certain embodiments, a glycovariant fusion protein of the disclosure comprises at least one glycosylated amino acid per each 10, 15, 20, 25, 30, 35, 40, 45, 50, 55, 60, 65, 70, 75, 80, 85, 90, 95, 100, 125, 150, or 200 amino acids. In certain embodiments, each N-linked glycosylated amino acid is separated by at least 10, 15, 20, 25, 30, 35, 40, 45, 50, 55, 60, 65, 70, 75, 80, 85, 90, 95, or 100 or more amino acids from any other N-linked, O-linked, or N-linked and O-linked glycosylated amino acid.

As used herein, a "glycosylation site" can mean a sugar attachment consensus sequence (i.e., a series of amino acids that act as a consensus sequence for attaching a sugar, either mono-, oligo-, or polysaccharides to an amino acid sequence) or it can mean the actual amino acid residue to which the sugar moiety is covalently linked. The sugar moiety can be a monosaccharide (simple sugar molecule), an oligosaccharide, or a polysaccharide.

N-linked glycosylation sites may be introduced into a fusion protein either by modifying the amino acid sequence of the protein or by chemically modifying an amino acid residue in the fusion protein to add a sugar moiety. In preferred embodiments, the fusion proteins described herein are modified to introduce (e.g., by insertion, deletion, or substitution of specified amino acids) at least one N-linked glycosylation site having the consensus sequence NXT/S (asparagine-X-serine/threonine), wherein X is any amino acid other than proline. Another means of increasing the number of carbohydrate moieties on a protein is by chemical or enzymatic coupling of glycosides to the polypeptide. For example, depending on the coupling mode used, a sugar moiety may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. See e.g., WO 87/05330 and Aplin and Wriston (1981) CRC Crit. Rev. Biochem., pp. 259-306, incorporated by reference herein. In exemplary embodiments, a sugar moiety is coupled to an arginine residue to produce an N-linked glycan.

In exemplary embodiments, sugar moieties are added to an introduced glycosylation site using the cellular machinery by expressing the fusion protein in a host cell. Generally, fusion proteins will be expressed in a mammalian cell line that provides proper glycosylation, such as HEK293 or CHO cell lines, or other mammalian expression cell lines.

In certain embodiments, sugar moieties may be added to an introduced glycosylation site using a non-mammalian host cell, such as a yeast, bacteria or insect cells, that has been engineered to produce mammalian-like glycosylation. Cell lines having genetically modified glycosylation pathways have been developed that carry out a sequence of enzyme reactions mimicking the processing of glycoproteins in humans. Recombinant proteins expressed in these engineered cells yield glycoproteins similar, if not substantially identical, to their human counterparts (e.g., mammalian-like glycosylation).

Techniques for genetically modifying host cells to alter the glycosylation profile of expressed peptides are well-known. See, e.g., Altmann et al. (1999, Glycoconjugate J. 16: 109-123), Ailor et al. (2000, Glycobiology 10(8): 837-847), Jarvis et al., (In vitrogen Conference, March, 1999, abstract), Hollister and Jarvis, (2001, Glycobiology 11(1): 1-9), and Palacpac et al., (1999, PNAS USA 96: 4697), Jarvis et al., (1998. Curr. Opin. Biotechnol. 9:528-533), Gemgross (U.S. Patent Publication No. 20020137134), all of which disclose techniques to "hummanize" insect or plant cell expression systems by transfecting insect or plant cells with glycosyltransferase genes.

Techniques also exist to genetically alter the glycosylation profile of peptides expressed in prokaryotic systems. *E. coli* has been engineered with various glycosyltransferases from the bacteria *Neisseria meningitidis* and *Azorhizobium* to produce oligosaccharides in vivo (Bettler et al., 1999, Glycoconj. J. 16:205-212). *E. coli* which has been genetically engineered to over-express *Neisseria meningitidis* β1,3 N acetyl glucoaminyltransferase lgta gene will efficiently glycosylate exogenous lactose (Priem et al., 2002, Glycobiology 12:235-240).

Fungal cells have also been genetically modified to produce exogenous glycosyltransferases (Yoshida et al., 1999, Glycobiology, 9(1):53-58; Kalsner et al., 1995, Glycoconj. J. 12:360-370; Schwientek and Ernst, 1994, Gene 145(2):299-303; Chiba et al, 1995, Biochem J. 308:405-409).

In certain embodiments, host cells expressing an Fc fusion protein of the disclosure may be a eukaryotic or prokaryotic cell expressing one or more exogenous glycosyltransferase enzymes and/or one or more exogenous glycosidase enzymes, wherein expression of a recombinant glycopeptide in the host cell results in the production of a recombinant glycopeptide having a "human" glycan structures.

In some embodiments the heterologous glycosyltransferase enzyme useful in the cell may be selected from a group consisting of any known glycosyltransferase enzyme included for example, in the list of Glycosyltransferase Families available in Taniguchi et al. (2002, Handbook of Glycosyltransferases and Related Genes, Springer, N.Y.).

In some embodiments, the host cell may be a eukaryotic or prokaryotic cell wherein one or more endogenous glycosyltransferase enzymes and/or one or more endogenous glycosidase enzymes have been inactivated such that expression of a recombinant glycopeptide in the host cell results in the production of a recombinant glycopeptide having a "human" glycan structure.

In some embodiments, the host cell may express heterologous glycosyltransferase enzymes and/or glycosidase enzymes while at the same time one or more endogenous glycosyltransferase enzymes and/or glycosidase enzymes are inactivated. Endogenous glycosyltransferase enzymes and/or glycosidase enzymes may be inactivated using any technique known to those skilled in the art including, but not limited to, antisense techniques and techniques involving insertion of nucleic acids into the genome of the host cell.

In exemplary embodiments, the glycovariant fusion proteins described herein have increased stability and/or an increased serum half life relative to the unmodified form of the fusion protein. In exemplary embodiments, the serum half life of the glycovariant fusion protein is increased by at least 10%, 15%, 20%, 25%, 30%, 40%, 50%, 55%, 60%, 70%, 75%, 80%, 85%, 90%, 95%, 100%, 125%, 150%, 200%, 250% or 300% or more relative to the unmodified form of the fusion protein. In certain embodiments, serum half-life of a modified Fc fusion protein and a fusion polypeptide lacking the additional glycosylation site are measured in the same animal model or species for comparison. In exemplary embodiments, the serum half-life is measured in a pharmacokinetic rat assay or a pharmacokinetic monkey assay as described herein (see e.g., Examples 4 and 5).

In exemplary embodiments, introduction of the one or more non-endogenous glycosylation sites does not significantly affect one or more biological activities of the heterologous polypeptide portion of the fusion protein. For example, one or more biological activities of the heterologous polypeptide portion of the fusion protein may be affected by less than 10-fold, 5-fold, 3-fold, 2.5-fold, 2-fold, 1.5-fold, 1-fold, 0.5-fold or less. Examples of biological activities of the heterologous polypeptide portion are described further herein and include for example, protein-protein interaction, ligand binding, physiological activity, etc.

In exemplary embodiments, one or more non-endogenous glycosylation sites are introduced into the heterologous portion of an Fc fusion protein. The heterologous portion of the Fc fusion protein may comprise a catalytic domain or a ligand binding domain. As used herein, a "ligand binding domain" refers to a region on a protein that interacts with another molecule, e.g., a ligand. For example, a ligand binding domain may refer to a region on a protein that is bound by an antibody, a region on an antibody that binds to an antigen, a region on a receptor that binds to a ligand, a region on a ligand that binds to a receptor, a region on a first polypeptide that binds to a second polypeptide, a region on a polypeptide that binds to a small molecule, etc. In exemplary embodiments, a ligand binding domain is a region in the extracellular domain of a transmembrane receptor protein that binds to a ligand. As used herein a "catalytic domain" refers to a region having a functional activity. Examples of catalytic domains include, for example, kinase domains, phosphatase domains, protease domains, etc.

In exemplary embodiments, one or more non-endogenous glycosylation sites are introduced into a surface exposed region that is flexible or unstructured, e.g., loop regions that connect α-helices and/or β-sheets. In general, a protein is a polypeptide chain having secondary and tertiary structure. The secondary structure of a polypeptide involves folding of a polypeptide chain into two common structural domains called α-helices and β-sheets. The tertiary structure of a protein consists of combinations of secondary structures, α-helices and β-sheets, connected by loop regions of various lengths and irregular shape. Generally, combinations of secondary structure elements form a stable hydrophobic core, while the loop regions are presented at the surface of the protein. As loop regions are solvent exposed, they are generally more susceptible to nucleophilic attack/peptide bond cleavage by various reactive molecules and protein enzymes (e.g., proteases) than the internal, structurally stable secondary structural domains (e.g., α-helix and β-sheet domains).

In certain embodiments, it may be desirable to remove one or more naturally occurring glycosylation sites (e.g., glycosylation sites in the unmodified form of the protein) in the heterologous polypeptide portion of the fusion protein. For example, in order to change the spacing of the N-linked glycosylation sites, it may be desirable to remove a naturally occurring glycosylation site and then introduce two non-endogenous glycosylation sites at desired locations. In addition, it may be desirable to remove one or more of the naturally occurring O-linked glycosylation sites occurring in the fusion protein.

N-linked and O-linked glycosylation sites may be removed by eliminating a consensus amino acid sequence or by chemical or enzymatic cleavage of the sugar moiety from the amino acid residue. For example, N-linked glycosylation sites may be removed by amino acid substitutions or deletions at one or both of the first or third amino acid positions of an N-linked glycosylation recognition site (i.e. NXT/S), and/or amino acid deletion at the second position of the tripeptide sequence. O-linked glycosylation sites may be removed by the addition, deletion, or substitution of one or more serine or threonine residues and/or the disruption of an O-linked consensus sequence as set forth below. Alternatively, removal of one or more naturally occurring carbohydrate moieties present on a polypeptide may be accomplished chemically and/or enzymatically. Chemical deglycosylation may involve, for example, exposure of a glycosylated polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on glycosylated polypeptides can be achieved by the use of a variety of endo- and exo-glycosidases as described by Thotakura et al. (1987) Meth. Enzymol. 138:350.

In certain embodiments, it may be desirable to introduce one or more O-linked glycosylation sites in addition to the one or more non-endogenous N-linked glycosylation sites. O-linked glycosylation sites may be added to protein by introducing an O-linked glycosylation consensus sequence into the polypeptide. Exemplary O-linked consensus sequences include, for example, CXXGGT/S-C (SEQ ID NO: 19), NSTE/DA (SEQ ID NO: 20), NITQS (SEQ ID NO: 21), QS1QS (SEQ ID NO: 22), 0/E-FI1RZK-V (SEQ ID NO: 23), C-E/D-SN, and GGSC-K/R (SEQ ID NO: 24). Alternatively, O-linked sugar moieties may be introduced by chemically modifying an amino acid in the polypeptide. See e.g., WO 87/05330 and Aplin and Wriston (1981) CRC Crit. Rev. Biochem., pp. 259-306, incorporated by reference herein.

In certain embodiments, the glycovariant polypeptides described herein may comprise additional domains, such as leader sequences, linkers, and/or purification/identification tags.

In some embodiments, fusion proteins may comprise a signal sequence, for example, a honey bee mellitin leader (HBML): MKFLVNVALVFMVVYISYIYA (SEQ ID NO: 10); Tissue Plasminogen Activator (TPA) leader: MDAMKRGLCCVLLLCGAVFVSP (SEQ ID NO: 11); or (iii) a native leader sequence.

Fusion proteins of the disclosure may optionally comprise a linker domain. In certain embodiments, fusion proteins comprise a relatively unstructured linker positioned between the Fc domain and the heterologous polypeptide domain. This unstructured linker may be an artificial sequence of 1, 2, 3, 4, or 5 amino acids, or a length between 5 and 10, 15, 20, 30, 50 or more amino acids, that are relatively free of secondary structure. A linker may be rich in glycine and proline residues and may, for example, contain a single sequence of threonine/serine and glycines or repeating sequences of threonine/serine and glycines (e.g., $TG_3$ (SEQ ID NO: 12) or $SG_3$ (SEQ ID NO: 13) singlets or repeats). In certain embodiments, one or more of the introduced glycosylation sites can be located in the linker domain Fusion proteins of the disclosure may include a domain that facilitates isolation and/or detection of the fusion protein. Well known examples of such domains include, but are not limited to, polyhistidine, Glu-Glu, glutathione S transferase (GST), thioredoxin, protein A, protein G, maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$ (SEQ ID NO: 25) fusion partners. As another example, a fusion domain may be selected so as to facilitate detection of the polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation.

It is understood that different elements of the fusion proteins may be arranged in any manner that is consistent with the desired functionality. For example, an Fc domain may be placed C-terminal to a heterologous polypeptide domain, or, alternatively, a heterologous polypeptide domain may be placed C-terminal to an Fc domain. The Fc domain and the heterologous domain need not be adjacent in a fusion protein, and additional domains or amino acid sequences may be included C- or N-terminal to either domain or between the domains.

In certain embodiments, the glycovariant fusion proteins may includes one or more additional modified amino acid residues selected from: a PEGylated amino acid, a farnesylated amino acid, an acetylated amino acid, a biotinylated amino acid, an amino acid conjugated to a lipid moiety, and an amino acid conjugated to an organic derivatizing agent. As a result of such post-translational modifications, the fusion proteins described herein may contain non-amino acid elements, such as polyethylene glycols, lipids, and phosphates. Different cells (such as CHO, HeLa, MDCK, 293, W138, NIH-3T3 or HEK293) have specific cellular machinery and characteristic mechanisms for such post-translational activities and may be chosen to ensure the correct modification and processing of the polypeptides of the invention. Fusion proteins of the disclosure are generally of higher molecular weight, being at least 30, 40, 50, 60, 70, 80, 90, 100, or 110 kDa, or more, in size.

In exemplary embodiments, the disclosure provides TNFR2-Fc glycovariant fusion proteins having at least one non-endogenous N-linked glycosylation sites outside of the Fc domain. In certain embodiments, a glycovariant fusion protein of the invention may comprises an amino acid sequence that is at least 75% identical to an amino acid sequence selected from SEQ ID NOs: 18, 21, 22, 23, or 24. In certain cases, the glycovariant fusion protein has an amino acid sequence at least 80%, 85%, 90%, 95%, 97%, 98%, 99% or 100% identical to an amino acid sequence selected from SEQ ID NOs: 18, 21, 22, 23, or 24.

In certain embodiments, the glycovariant Fc fusion proteins described herein do not contain an extracellular domain of an ActRIIb receptor and/or a variable region of an antibody.

Fc Domains

The glycovariant fusion proteins described herein comprise an immunoglobulin heavy chain Fc domain fused to a heterologous polypeptide. Fusions with the Fc portion of an immunoglobulin are known to confer desirable pharmacokinetic properties on a wide range of proteins. The term "Fc region" or "Fc domain" as used herein refers to a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus of the immunoglobulin. The C-terminal lysine (residue 447 according to the EU numbering system) of the Fc region may be removed, for example, when recombinantly engineering the nucleic acid encoding a heavy chain of the antibody. Unless indicated otherwise, herein the numbering of the residues in an immunoglobulin heavy chain is that of the EU index as in Kabat et al., Sequences of Proteins of Immunological Interest, 5th Ed. Public Health Service, National Institutes of Health, Bethesda, (1991), expressly incorporated herein by reference. The "EU index as in Kabat" refers to the residue numbering of the human IgG1 EU antibody.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

In preferred embodiments, the Fc fusion protein described herein have a heterologous portion fused to the N-terminus of the C-terminal portion of an immunoglobuline Fc domain. Preferably, a sequence beginning in the hinge region just upstream of the papain cleavage site, e.g. taking the first residue of heavy chain constant region to be 114 or analogous sites of other immunoglobulins, is used in the fusion. In one embodiment, the heterologous domain is fused to the hinge region and CH2 and CH3 or CH1, hinge, CH2 and CH3 domains of an IgG1, IgG2, or IgG3 heavy chain. In some embodiments, the precise site at which the fusion is made is not critical, and the optimal site can be determined by routine experimentation.

For human Fc domains, the use of human IgG1 and IgG3 immunoglobulin sequences is preferred. A major advantage of using IgG1 is that an IgG1 fusion protein can be purified efficiently on immobilized protein A. In contrast, purification of IgG3 fusion proteins requires protein G, a significantly less versatile medium. However, other structural and functional properties of immunoglobulins should be considered when choosing the Ig fusion partner for a particular construction. For example, the IgG3 hinge is longer and more flexible, so it can accommodate a larger heterologous portion that may not fold or function properly when fused to IgG1. Another consideration may be valency; IgG immunoadhesins are bivalent homodimers, whereas Ig subtypes like IgA and IgM may give rise to dimeric or pentameric structures, respectively, of the basic Ig homodimer unit.

For Fc fusion proteins designed for in vivo application, the pharmacokinetic properties and the effector functions specified by the Fc region are important as well. Although IgG1, IgG2 and IgG4 all have in vivo half-lives of 21 days, their relative potencies at activating the complement system are different. IgG4 does not activate complement, and IgG2 is significantly weaker at complement activation than IgG1. Moreover, unlike IgG1, IgG2 does not bind to Fc receptors on mononuclear cells or neutrophils. While IgG3 is optimal for complement activation, its in vivo half-life in approximately one third of the other IgG isotypes.

Another important consideration for Fc fusion proteins designed to be used as human therapeutics is the number of allotypic variants of the particular isotype. In general, IgG isotypes with fewer serologically-defined allotypes are preferred. For example, IgG1 has only four serologically-defined allotypic sites, two of which (G1m and 2) are located in the Fc region; and one of these sites G1m1, is non-immunogenic. In contrast, there are 12 sero logically-defined allotypes in IgG3, all of which are in the Fc region; only three of these sites (G3 m5, 11 and 21) have one allotype which is non-immunogenic. Thus, the potential immunogenicity of an IgG3 fusion protein is greater than that of an IgG1 fusion protein.

In certain embodiments, an Fc domain used in the Fc fusion proteins may comprise one or more alterations as compared to the wild-type Fc domain. These Fc domains would nonetheless retain substantially the same characteristics required for therapeutic utility as compared to their wild-type counterpart. For example, it is thought that certain alterations can be made in the Fc region that would result in altered (i.e., either improved or diminished) CIq binding and/or Complement Dependent Cytotoxicity (CDC), e.g., as described in WO99/51642. See also Duncan & Winter Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc reg on with one or more substitutions therein which improve binding of the Fc region to FcRn. Polypeptide variants with altered Fc region amino acid sequences and increased or decreased CIq binding capability are described in U.S. Pat. No. 6,194,551 and the International Publication WO99/51642. See, also, Idusogie et al. J. Immunol. 164: 4178-4184 (2000). The contents of these are specifically incorporated herein by reference.

An exemplary Fc domain is shown below.

```
                                            (e.g., SEQ ID NO: 14)
THTCPPCPAPELLGGPSVFLFPPKPKDTLMISRTPEVTCVVVD(A)

VSHEDPEVKFNWYVDGVEVHNAKTKPREEQYNSTYRVVSVLTVLHQ

DWLNGKEYKCK(A)VSNKALPVPIEKTISKAKGQPREPQVYTLPPS

REEMTKNQVSLTCLVKGFYPSDIAVEWESNGQPENNYKTTPPVLDS

DGPFFLYSKLTVDKSRWQQGNVFSCSVMHEALHN(A)HYTQKSLSL

SPGK*
```

An example of an advantageous linker (TG$_3$ (SEQ ID NO: 12)) and Fc domain combined is shown below:

```
                                            (SEQ ID NO: 18)
TGGGTHTCPPCPAPELLGGPSVFLFPPKPKDTLMISRTPEVTCVVV

DVSHEDPEVKFNWYVDGVEVHNAKTKPREEQYNSTYRVVSVLTVLH

QDWLNGKEYKCKVSNKALPAPIEKTISKAKGQPREPQVYTLPPSRE

EMTKNQVSLTCLVKGFYPSDIAVEWESNGQPENNYKTTPPVLDSDG

SFFLYSKLTVDKSRWQQGNVFSCSVMHEALHNHYTQKSLSLSPGK
```

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the MHC class I-related Fc-receptor (FcRN) relative to a wild-type Fc domain.

Heterologous Polypeptides

The glycovariant fusion proteins described herein also comprise a heterologous polypeptide portion fused either directly or indirectly to the Fc domain. The heterologous polypeptide portion may be any polypeptide. In exemplary embodiments the heterologous polypeptide portion has a molecular weight of at least 10, 15, 20, 25, 30, 35, 40, 50, 60, 70, 80, 90 or 100 kDa or greater.

Heterologous polypeptide portions may be a therapeutic protein, or fragments thereof, such as growth factors, enzymes, serum enzymes, endocrine factors such as GLP1, bone morphogenetic proteins and soluble receptor fragments.

Exemplary heterologous polypeptides include growth factors, such as hepatocyte growth factor (HGF), nerve growth factors (NGF), epidermal growth factors (EGF), fibroblast growth factors (FGF), transforming growth factors (e.g., TGF-alpha, TGF-beta, TGF-beta2, TGF-beta3), vascular endothelial growth factors (VEGF; e.g., VEGF-2), interferons (e.g., INF-alpha, INF-beta) and insulin. Other exemplary heterologous polypeptides include enzymes, such as alpha-galactosidase (e.g., Fabrazyme™) Other exemplary heterologous polypeptides include bone morphogenetic proteins (BMP), erythropoietins (EPO), myostatin, and tumor necrosis factors (e.g., TNF-α). Other exemplary heterologous polypeptides include extracellular domains of transmembrane receptors, including any naturally occurring extracellular domain of a cellular receptor as well as any variants thereof (including mutants, fragments and peptidomimetic forms).

In exemplary embodiments, the heterologous polypeptide portion is an extracellular domain of a receptor from the TNF/NGF family of receptors. Examples of soluble receptor polypeptides include, for example, SEQ ID NOs: 2, 5, 6, 7, or 8 of the disclosure. In preferred embodiments, an extracellular receptor domain included in the glycovariant fusion proteins having at least one non-endogenous N-linked glycosylation site retains the ability to bind a ligand of the naturally occurring receptor. In certain embodiments, a non-endogenous N-linked glycosylation site is introduced outside of the ligand binding pocket of the extracellular receptor domain. Preferably, glycosylation of the introduced glycosylation site does not significantly affect the binding of the receptor protein to the soluble ligand. In exemplary embodiments, glycosylation of the introduced glycosylation sited does not reduce binding of the extracellular receptor domain to its ligand by more than 10-fold, 5-fold, 3-fold, 2.5-fold, 2-fold, 1.5-fold, 1-fold, 0.5-fold, or less. Preferably, a soluble receptor domain comprising at least one non-endogenous N-linked glycosylation site will bind to a specified ligand with a dissociation constant of less than 1 μM or less than 100, 10, or 1 nM.

In one embodiment, the glycovariant fusion proteins described herein comprises a heterologous polypeptide portion that comprises an extracellular domain of a receptor from the nerve growth factor (NGF)/tumor necrosis factor (TNF) receptor family. See e.g., M. Lotz, et al., J. Leukocyte Biology, 60:1-7 (1990). The NGF/TNF receptor family includes, for example, nerve growth factor receptor (NGFR), TNFR1 (or TNFR55), TNFR2 (or TNFR75), the TNF receptor-related protein (TNFRrp), CD40, the Hodgkin's antigen CD30, the T cell antigen CD27, Fas/APO-1, OX-40, and 4-1BB/ILA. In exemplary embodiments, the fusion proteins described herein comprise an extracellular domain of TNFR2 having at least one non-endogenous N-linked glycosylation site.

As used herein, the term "TNFR2" refers to a family of tumor necrosis factor receptor type 2 (TNFR2) proteins from any species and variants derived from such TNFR2 proteins by mutagenesis or other modification. Members of the TNFR2 family are generally transmembrane proteins, composed of a ligand-binding extracellular domain with a cysteine-rich region, a transmembrane domain, and a cytoplasmic domain with predicted intracellular signaling activity.

The term "TNFR2 polypeptide" includes polypeptides comprising any naturally occurring polypeptide of a TNFR2 family member as well as any variants thereof (including mutants, fragments, fusions, and peptidomimetic forms) that retain a useful activity. For example, TNFR2 polypeptides include polypeptides derived from the sequence of any known TNFR2 having a sequence at least about 80% identical to the sequence of an TNFR2 polypeptide, and preferably at least 85%, 90%, 95%, 97%, 99% or greater identity. For example, a TNFR2 polypeptide of the invention may bind to TNF$\alpha$ or TNF$\beta$ and inhibit the function of a TNFR2 protein and/or TNF$\alpha$ or TNF$\beta$. Examples of TNFR2 polypeptides include human TNFR2 precursor polypeptide (SEQ ID NO:1) and soluble human TNFR2 polypeptides (e.g., SEQ ID NOs: 2, 5, 6, 7, or 8).

The human TNFR2 precursor protein sequence is as follows:

(SEQ ID NO: 1)

MAPVAVWAAL AVGLELWAAA HALPAQVAFT PYAPEPGSTC

RLREYYDQTA QMCCSKCSPG QHAKVFCTKT SDTVCDSCED

STYTQLWNWV PECLSCGSRC SSDQVETQAC TREQNRICTC

RPGWYCALSK QEGCRLCAPL RKCRPGFGVA RPGTETSDVV

CKPCAPGTFS NTTSSTDICR PHQICNVVAI PGNASMDAVC

TSTSPTRSMA PGAVHLPQPV STRSQHTQPT PEPSTAPSTS

FLLPMGPSPP AEGSTGDEPK SCDKTHTCPP CPAPELLGGP

SVFLFPPKPK DTLMISRTPE VTCVVVDVSH EDPEVKFNWY

VDGVEVHNAK TKPREEQYNS TYRVVSVLTV LHQDWLNGKE

YKCKVSNKAL PAPIEKTISK AKGQPREPQV YTLPPSREEM

TKNQVSLTCL VKGFYPSDIA VEWESNGQPE NNYKTTPPVL

DSDGSFFLYS KLTVDKSRWQ QGNVFSCSVM HEALHNHYTQ

KSLSLSPGK*

The signal peptide is single underlined; the extracellular domain is in bold and the potential N-linked glycosylation sites are double underlined.

The human TNFR2 soluble (extracellular), processed polypeptide sequence is as follows:

(SEQ ID NO: 2)

LPAQVAFTPY APEPGSTCRL REYYDQTAQM CCSKCSPGQH

AKVFCTKTSD TVCDSCEDST YTQLWNWVPE CLSCGSRCSS

DQVETQACTR EQNRICTCRP GWYCALSKQE GCRLCAPLRK

CRPGFGVARP GTETSDVVCK PCAPGTFS*N*T TSSTDICRPH

QICNVVAIPG *N*ASMDAVCTS TSPTRSMAPG AVHLPQPVST

RSQHTQPTPE PSTAPSTSFL LPMGPSPPAE GSTGD

Naturally occurring N-linked glycosylation sites are underlined. As reported herein, the amino terminal leucine may be eliminated, leaving a proline residue at the amino-terminus.

The nucleic acid sequence encoding human TRFR2 precursor protein is as follows (Genbank entry NM_001066.2):

(SEQ ID NO: 3)

ATGGCGCCCG TCGCCGTCTG GGCCGCGCTG GCCGTCGGAC

TGGAGCTCTG GGCTGCGGCG CACGCCTTGC CCGCCCAGGT

GGCATTTACA CCCTACGCCC CGGAGCCCGG GAGCACATGC

CGGCTCAGAG AATACTATGA CCAGACAGCT CAGATGTGCT

```
GCAGCAAATG CTCGCCGGGC CAACATGCAA AAGTCTTCTG
TACCAAGACC TCGGACACCG TGTGTGACTC CTGTGAGGAC
AGCACATACA CCCAGCTCTG GAACTGGGTT CCCGAGTGCT
TGAGCTGTGG CTCCCGCTGT AGCTCTGACC AGGTGGAAAC
TCAAGCCTGC ACTCGGGAAC AGAACCGCAT CTGCACCTGC
AGGCCCGGCT GGTACTGCGC GCTGAGCAAG CAGGAGGGGT
GCCGGCTGTG CGCGCCGCTG CGCAAGTGCC GCCCGGGCTT
CGGCGTGGCC AGACCAGGAA CTGAAACATC AGACGTGGTG
TGCAAGCCCT GTGCCCCGGG GACGTTCTCC AACACGACTT
CATCCACGGA TATTTGCAGG CCCCACCAGA TCTGTAACGT
GGTGGCCATC CCTGGGAATG CAAGCATGGA TGCAGTCTGC
ACGTCCACGT CCCCCACCCG GAGTATGGCC CCAGGGGCAG
TACACTTACC CCAGCCAGTG TCCACACGAT CCCAACACAC
GCAGCCAACT CCAGAACCCA GCACTGCTCC AAGCACCTCC
TTCCTGCTCC CAATGGGCCC CAGCCCCCCA GCTGAAGGGA
GCACTGGCGA CTTCGCTCTT CCAGTTGGAC TGATTGTGGG
TGTGACAGCC TTGGGTCTAC TAATAATAGG AGTGGTGAAC
TGTGTCATCA TGACCCAGGT GAAAAGAAG CCCTTGTGCC
TGCAGAGAGA AGCCAAGGTG CCTCACTTGC CTGCCGATAA
GGCCCGGGGT ACACAGGGCC CCGAGCAGCA GCACCTGCTG
ATCACAGCGC CGAGCTCCAG CAGCAGCTCC CTGGAGAGCT
CGGCCAGTGC GTTGGACAGA AGGGCGCCCA CTCGGAACCA
GCCACAGGCA CCAGGCGTGG AGGCCAGTGG GGCCGGGGAG
GCCCGGGCCA GCACCGGGAG CTCAGATTCT TCCCCTGGTG
GCCATGGGAC CCAGGTCAAT GTCACCTGCA TCGTGAACGT
CTGTAGCAGC TCTGACCACA GCTCACAGTG CTCCTCCCAA
GCCAGCTCCA CAATGGGAGA CACAGATTCC AGCCCCTCGG
AGTCCCCGAA GGACGAGCAG GTCCCCTTCT CCAAGGAGGA
ATGTGCCTTT CGGTCACAGC TGGAGACGCC AGAGACCCTG
CTGGGGAGCA CCGAAGAGAA GCCCCTGCCC CTTGGAGTGC
CTGATGCTGG GATGAAGCCC AGTTAA.
```

The nucleic acid sequence encoding a human TNFR2 soluble (extracellular) polypeptide is as follows:

```
                                        (SEQ ID NO: 4)
TTGC CCGCCCAGGT GGCATTTACA CCCTACGCCC
CGGAGCCCGG GAGCACATGC CGGCTCAGAG AATACTATGA
CCAGACAGCT CAGATGTGCT GCAGCAAATG CTCGCCGGGC
CAACATGCAA AAGTCTTCTG TACCAAGACC TCGGACACCG
TGTGTGACTC CTGTGAGGAC AGCACATACA CCCAGCTCTG
GAACTGGGTT CCCGAGTGCT TGAGCTGTGG CTCCCGCTGT
AGCTCTGACC AGGTGGAAAC TCAAGCCTGC ACTCGGGAAC
AGAACCGCAT CTGCACCTGC AGGCCCGGCT GGTACTGCGC
GCTGAGCAAG CAGGAGGGGT GCCGGCTGTG CGCGCCGCTG
CGCAAGTGCC GCCCGGGCTT CGGCGTGGCC AGACCAGGAA
CTGAAACATC AGACGTGGTG TGCAAGCCCT GTGCCCCGGG
GACGTTCTCC AACACGACTT CATCCACGGA TATTTGCAGG
CCCCACCAGA TCTGTAACGT GGTGGCCATC CCTGGGAATG
CAAGCATGGA TGCAGTCTGC ACGTCCACGT CCCCCACCCG
GAGTATGGCC CCAGGGGCAG TACACTTACC CCAGCCAGTG
TCCACACGAT CCCAACACAC GCAGCCAACT CCAGAACCCA
GCACTGCTCC AAGCACCTCC TTCCTGCTCC CAATGGGCCC
CAGCCCCCCA GCTGAAGGGA GCACTGGCGA C.
```

The disclosure demonstrates that the addition of one or more N-linked glycosylation sites (NXS/T) increases the serum half-life of a TNFR2-Fc fusion protein relative an unmodified TNFR2-Fc protein. N-linked glycosylation sites may be introduced with minimal effort by introducing an N in the correct position with respect to a pre-existing S or T, or by introducing an S or T at a correct position with respect to a pre-existing N. Particularly suitable sites for the introduction of non-endogenous NXS/T sequences in TNFR2 include, for example, amino acids 25-27 (DQT), 26-28 (QIA), 133-135 (ETS), and 231-233 (GST) in relation to SEQ ID NO: 2. For example, desirable alterations that would introduce an N-linked glycosylation site are: D25N, Q26N, A28S, E133N, and G231N. In some instances, several amino acids may be modified to introduce a non-endogenous NXS/T sequence. For example, a double substitution of Q26N/A28S provides both the N and S residues necessary to introduce a novel N-linked glycosylation site at residues 26-28 of SEQ ID NO: 2. Furthermore, more than one region on the TNFR2-Fc polypeptide may be modified to introduce multiple N-linked glycosylation sites including. For example, a double substitution of D25N/E133N introduces two N-linked glycosylation sites at residues 25-27 and 133-135 of SEQ ID NO: 2 and a double substitution of D25N/G231N introduces two N-linked glycosylation sites at residues 25-27 and 231-233 of SEQ ID NO: 2. Other exemplary TNFR2 variants include, for example, E133N/G231N, Q26N/A28S/E133N and Q26N/A28S/G231N. Any S that is predicted to be glycosylated may be altered to a T without creating an immunogenic site, due to the protection afforded by the glycosylation. Similarly, any T that is predicted to be glycosylated may be altered to and S.

3. Nucleic Acids Encoding Glycovariant Fusion Proteins

In certain aspects, the invention provides isolated and/or recombinant nucleic acids encoding any of the glycovariant fusion proteins of the invention, including fragments and functional variants disclosed herein. The subject nucleic acids may be single-stranded or double-stranded. Such nucleic acids may be DNA or RNA molecules. These nucleic acids may be used, for example, in methods for making glycovariant fusion proteins of the invention or as direct therapeutic agents (e.g., in a gene therapy approach).

In exemplary embodiments, a nucleic acid of the invention encodes a TNFR2-Fc glycovariant fusion protein. For example, SEQ ID NO: 3 encodes the naturally occurring human TNFR2 precursor polypeptides, while SEQ ID NO: 4 encodes the processed extracellular domain of TNFR2.

In certain embodiments, the subject nucleic acids encoding glycovariant fusion proteins of the invention are further understood to include nucleic acids that are variants of SEQ ID NO: 3, 4, 9, or 17. Variant nucleotide sequences include sequences that differ by one or more nucleotide substitutions, additions or deletions, such as allelic variants. In exemplary embodiments, the variant nucleic acids comprise a nucleic acid sequence modification that results in the introduction of one or more non-endogenous N-linked glycosylation sites in the encoded protein.

In certain embodiments, the invention provides isolated or recombinant nucleic acid sequences that are at least 80%, 85%, 90%, 95%, 97%, 98%, 99% or 100% identical to SEQ ID NO: 3, 4, 9, or 17, and include one or more sequence modifications that result in the introduction of a non-endogenous N-linked glycosylation site in the encoded protein. One of ordinary skill in the art will appreciate that nucleic acid sequences complementary to SEQ ID NO: 3, 4, 9, or 17, and variants of SEQ ID NO: 3, 4, 9, or 17 that introduce one or more non-endogenous N-linked glycosylation site in the encoded protein are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 3, 4, 9, or 17, complement sequence of SEQ ID NO: 3, 4, 9, or 17, or fragments thereof. Such nucleotide sequences encode glycovariant protein fusions having one or more non-endogenous N-linked glycosylation sites. One of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids variants which differ from the nucleic acids as set forth in SEQ ID NOs: 3, 4, or 9 due to degeneracy in the genetic code and that introduce one or more non-endogenous N-linked glycosylation site in the encoded protein are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain embodiments, the subject nucleic acid is provided in an expression vector comprising a nucleotide sequence encoding a glycovariant fusion protein of the invention and operably linked to at least one regulatory sequence. Regulatory sequences are art-recognized and are selected to direct expression of a polypeptide of the invention. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding a glycovariant fusion protein. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast alpha-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant glycovariant fusion protein of the invention include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 3rd Ed., ed. by Sambrook, Fritsch and Maniatis (Cold Spring Harbor Laboratory Press, 2001). In some instances, it may be desirable to express the recombinant glycovariant fusion proteins by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject glycovariant fusion proteins of the invention in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject glycovariant fusion proteins in cells propagated in culture, e.g., to produce proteins, including fusion proteins or variant proteins, for purification.

This disclosure also pertains to a host cell transfected with a recombinant gene including a coding sequence for one or more of the subject glycovariant protein fusions of the invention. The host cell may be any prokaryotic or eukaryotic cell. For example, a glycovariant fusion protein of the invention may be expressed in bacterial cells such as *E. coli*, insect cells (e.g., using a baculovirus expression system), yeast, or mammalian cells. Other suitable host cells are known to those skilled in the art. Preferably, the host cell will be a mammalian host cell, such as a CHO or BHK cell line, that will produce a mammalian glycosylation pattern on the expressed protein.

Accordingly, the present invention further pertains to methods of producing the subject glycovariant fusion proteins of the invention. For example, a host cell transfected with an expression vector encoding an Fc-fusion protein can be cultured under appropriate conditions to allow expression of the Fc-fusion protein to occur. The Fc-fusion protein may be secreted and isolated from a mixture of cells and medium containing the Fc-fusion protein. Alternatively, the Fc-fusion protein may be retained cytoplasmically or in a membrane fraction and the cells harvested, lysed and the protein isolated. A cell culture includes host cells, media and other byproducts. Suitable media for cell culture are well known in the art. The subject Fc-fusion proteins can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the Fc-fusion proteins and affinity purification with an agent that binds to a domain fused to the Fc-fusion protein (e.g., a protein A column may be used to purify an Fc-fusion proteins). In a preferred embodiment, the Fc-fusion protein comprises an additional domain which facilitates its purification. In a preferred embodiment, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. Glycovariant fusion proteins of the invention may be purified to a purity of >98% as determined by size exclusion chromatography and >95% as determined by SDS PAGE.

In another embodiment, a fusion gene coding for a purification leader sequence, such as a poly-(His)/enterokinase cleavage site sequence at the N-terminus of the desired portion of the recombinant glycovariant Fc-fusion protein of the invention, can allow purification of the expressed fusion protein by affinity chromatography using a $Ni^{2+}$ metal resin. The purification leader sequence can then be subsequently removed by treatment with enterokinase to provide the purified glycovariant fusion protein of the invention (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

4. Methods of Increasing Serum Half Life

In specific embodiments, the invention relates to methods for increasing the stability and/or half-life (e.g. in vitro, in vivo, or serum half-life) of an Fc fusion protein by modifying the fusion protein to introduce one or more non-endogenous N-linked glycosylation sites outside of the Fc domain. For example, such a method may include modifying the sequence of an Fc fusion protein to introduce one or more non-endogenous N-linked glycosylation site and expressing a nucleic acid encoding said modified polypeptide in a suitable cell, such as a Chinese hamster ovary (CHO) cell or a human cell to produce a glycovariant Fc fusion protein. Such a method may comprise: a) culturing a cell under conditions suitable for expression of the modified polypeptide, wherein said cell is transformed with a modified polypeptide expression construct; and b) recovering the modified protein so expressed. Purification may be achieved by a series of purification steps, including for example, one, two, or three or more of the following, in any order: protein A chromatograph, anion exchange chromotography (e.g., Q sepharose), hydrophobic interaction chromotography (e.g., phenylsepharose), size exclusion chromatography, and cation exchange chromatography. Such polypeptide of the disclosure may be further formulated in liquid or solid (e.g., lyophilized forms). Any of the glycovariant fusion proteins described herein may be produced using the said method.

In preferred embodiments, glycosylation at one or more of the introduced glycosylations sites increases the half-life (e.g., in vitro, in vivo, serum half-life) of the modified fusion protein by at least 10%, 25%, 50%, 75%, 100%, 125%, 150%, 175%, 200%, 225%, or 250% or more relative to the serum half-life of the fusion protein lacking the introduced glycosylation site. In certain embodiments, the methods of the disclosure may be used introduce at least one glycosylated amino acid per each 10, 20, 30, 40, 50, 60, 70, 80, 90, 100, 110, 120, 130, 140, 150, 160, 170, 180, 190, or 200 amino acids of fusion proteins of the disclosure. In certain embodiments, the methods of the disclosure may be used introduce glycosylation sites so as to maintain a separation between each amino acid modified by an N-linked glycosylation, an O-linked glycosylation, or both, by at least 10, 20, 30, 40, 50, 60, 70, 80, 90, or 100 or more amino acids.

In certain embodiments, the disclosure provides methods for extending the half-life of a fusion protein comprising at least one heterologous polypeptide domain and an immunoglobulin Fc domain. For example, such methods may include a) modifying an Fc-fusion protein outside of the immunoglobulin Fc domain to introduce one or more non-endogenous N-linked glycosylation sites and b) expressing the Fc-fusion protein such that one of the introduced glycosylation sites are glycosylated. The methods disclosed herein may be used, for example, to extend the half-life of an Fc-fusion protein comprising a portion of an extracellular domain (e.g., soluble portion) of a receptor that includes a ligand-binding domain. In certain embodiments, the methods are used to introduce glycosylation sites outside of the ligand-binding domain of the Fc-fusion protein. In preferred embodiments, the methods for introducing glycosylation sites do not significantly affect the binding of the receptor portion of the fusion protein to the soluble ligand, e.g., ligand binding is affected by less than 2-, 3-, 5-, 10-, or 15-fold relative to ligand binding to the Fc-fusion protein lacking the introduced glycosylation site. In some embodiments, the methods of the disclosure are used to introduce one or more glycosylation sites on fusion proteins comprising a linker domain. In certain embodiments, the methods of the disclosure may be used to introduce at least one glycosylation site within the linker domain. Generally, the methods disclosed herein are used to increase the half-life of fusion proteins having heterologous domains that are of higher molecular weight, e.g., proteins of higher molecular being at least 25, 30, 35, 40, 45, 50, 55, 60, 65, 70, 75, 80, 85, 90, 95, 100, 105, or 110 kDa.

5. Screening Assays

In certain aspects, the present invention provides screening assays for identifying glycovariant Fc fusion proteins that maintain at least one biological activity and have increased stability and/or increased serum half life. Glycovariant fusion proteins can be tested to assess their ability to modulate biological activities, to assess their stability and/or to assess their serum half life in vivo or in vitro. Glycovariant fusion proteins can be tested, for example, in animal models.

There are numerous approaches to screening for biological activity of a glycovariant fusion protein of the invention, for example, when assaying a glycovariant receptor-Fc fusion protein, the ability of the modified receptor to bind to a ligand may be determined, or the ability of the glycovariant fusion protein to disrupt ligand-receptor signaling may also be assayed. In certain embodiments, high-throughput screening of glycovariant fusion proteins can be carried out to identify glycovariants that retain at least one biological activity of the unmodified protein, such as, for example, receptor variants that perturb ligand or receptor-mediated effects on a selected cell line.

A variety of assay formats will suffice and, in light of the present disclosure, those not expressly described herein will nevertheless be comprehended by one of ordinary skill in the art. As described herein, glycovariant fusion proteins of the invention can be obtained by screening polypeptides recombinantly produced from the corresponding fragment of the nucleic acid encoding said fusion proteins. In addition, fragments can be chemically synthesized using techniques known in the art such as conventional Merrifield solid phase f-Moc or t-Boc chemistry.

Functionally active glycovariant fusion proteins of the invention can be obtained by screening libraries of modified fusion proteins recombinantly produced from the corresponding mutagenized nucleic acids encoding said fusion proteins. The glycovariants can be produced and tested to identify those that retain at least biological activity of the unmodified fusion proteins, for example, the ability of a glycovariant receptor fusion to act as an antagonist (inhibitor) of various cellular receptor proteins (e.g., TNFR2 receptor proteins) and/or intracellular signaling mediated by a ligand-receptor binding.

Functional glycovariants may be generated by modifying the amino acid sequence of a fusion protein of the invention to increase stability and/or serum half life. Such modified glycovariant proteins when selected to retain a biological activity, such as, for example, ligand binding, are considered functional equivalents of the unmodified fusion proteins. Modified glycovariant fusion proteins can also be produced, for instance, by amino acid substitution, deletion, or addition to introduce one or more N-linked glycosylation sites and/or other sequence modifications, such as conservative substitutions. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a fusion protein of the invention results in a functional homolog can be readily determined by assessing the ability of the variant fusion protein to exhibit a biological activity in a fashion similar to the unmodified fusion protein. For example, variant receptor Fc fusion proteins, such as a TNFR2-Fc fusion protein, may be screened for ability to bind to a specific ligand (e.g., TNFα or TNFβ), to prevent binding of a ligand to a receptor polypeptide or to interfere with signaling caused by ligand binding to the receptor.

A combinatorial library of glycovariant fusion proteins may be produced by way of a degenerate library of genes encoding a library of fusion proteins which each include at least a portion of potential polypeptide sequences. For instance, a mixture of synthetic oligonucleotides can be enzymatically ligated into gene sequences such that the degenerate set of potential polypeptide nucleotide sequences are expressible as individual polypeptides, or alternatively, as a set of larger fusion proteins (e.g., for phage display).

There are many ways by which the library of potential glycovariants can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of glycovariant fusion proteins of the invention. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

Preferred assays include receptor-ligand binding assays and ligand-mediated cell signaling assays. Complex formation between glycovariant receptor-Fc fusion proteins of the invention and ligands may be detected by a variety of techniques. For instance, modulation of the formation of complexes can be quantitated using, for example, detectably labeled proteins such as radiolabeled (e.g., $^{32}$P, $^{35}$S, $^{14}$C or $^{3}$H), fluorescently labeled (e.g., FITC), or enzymatically labeled receptor polypeptide or ligands, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a glycovariant receptor-Fc fusion protein and its binding ligand. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between a glycovariant Fc fusion protein and its binding partner. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). Alternatively, such protein-protein interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, glycovariant fusion proteins may be screened in a mechanism based assay, such as an assay to detect glycovariant fusion proteins which bind to a ligand or receptor polypeptide. This may include a solid phase or fluid phase binding event. Alternatively, the gene encoding a ligand or receptor polypeptide can be transfected with a reporter system (e.g., β-galactosidase, luciferase, or green fluorescent protein) into a cell and screened against the glycovariant library optionally by a high throughput screening or with individual members of the glycovariant library. Other mechanism based binding assays may be used, for example, binding assays which detect changes in free energy. Binding assays can be performed with the target fixed to a well, bead or chip or captured by an immobilized antibody or resolved by capillary electrophoresis. The bound proteins may be detected usually using colorimetric or fluorescence or surface plasmon resonance.

6. Exemplary Therapeutic Uses

In various embodiments, patients being treated with a glycovariant fusion protein of the invention, or candidate patients for treatment with a glycovariant fusion protein of the invention, may be mammals such as rodents and primates, and particularly human patients. In certain embodiments, the disclosure provides modified soluble receptor-Fc fusions characterized by an increased half-life. Receptor-Fc fusions have been previously described for use in treating a variety of disorders and conditions, which are summarized herein.

As used herein, a therapeutic that "prevents" a disorder or condition refers to a therapeutic that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established. In either case, prevention or treatment may be discerned in the diagnosis provided by a physician or other health care provider and the intended result of administration of the therapeutic agent.

In some embodiments, the disclosure provides a glycovariant fusion protein comprising an extracellular domain of a TNFR2 receptor having an increased serum half life. Such TNFR2-Fc glycovariant fusions may be used to prevent or treat a variety of TNFα-mediated disorders or conditions including, for example acute and chronic immune and autoimmune pathologies (e.g., systemic lupus erythematosus (SLE), rheumatoid arthritis, juvenile chronic arthritis, thyroidosis, graft versus host disease, scleroderma, diabetes mellitus, Graves' disease), spondyloarthropathies, disorders associated with infection (e.g., sepsis syndrome, cachexia, circulatory collapse and shock resulting from acute or chronic bacterial infection, acute and chronic parasitic and/or infectious diseases, bacterial, viral or fungal), chronic inflammatory pathologies (e.g., scleroderma, sarcoidosis, chronic inflammatory bowel disease, ulcerative colitis, and Crohn's pathology), vascular inflammatory pathologies (e.g., disseminated intravascular coagulation, atherosclerosis, and Kawasaki's pathology), and neurodegenerative diseases (e.g., multiple sclerosis, acute transverse myelitis, extrapyramidal, Huntington's Chorea and senile chorea; Parkinson's disease, Progressive supranucleo palsy, spinal ataxia, Friedreich's ataxia, Mencel, Dejerine-Thomas, Shi-Drager, MachadoJoseph, Refsum's disease, abetalipoprotemia, telangiectasia, mitochondrial multi-system disorder, amyotrophic lateral sclerosis, infantile spinal muscular atrophy, juvenile spinal muscular atrophy, Alzheimer's disease, Down's Syndrome, Diffuse Lewy body disease, Wernicke-Korsakoff syndrome, Creutzfeldt-Jakob disease, Subacute sclerosing panencephalitis, Hallerrorden-Spatz disease, and Dementia pugilistica).

7. Pharmaceutical Compositions

In certain embodiments, the glycovariant fusion proteins described herein are formulated with a pharmaceutically acceptable carrier. For example, a fusion protein of the disclosure can be administered alone or as a component of a pharmaceutical formulation (therapeutic composition). The subject compounds may be formulated for administration in any convenient way for use in human or veterinary medicine. An appropriate dosage regimen may be determined by an attending physician and may be informed by the standard dosage regimen for the unmodified version of the therapeutic protein.

In certain embodiments, a therapeutic method of the invention includes administering the composition systemically, or locally as an implant or device. When administered, the therapeutic composition for use in this invention is, of course, in a pyrogen-free, physiologically acceptable form. Therapeutically useful agents other than the fusion proteins described herein which may optionally be included in the composition as described above, may be administered simultaneously or sequentially with the subject fusion proteins in the methods of the invention.

Typically, the fusion proteins described herein will be administered parentally. Pharmaceutical compositions suitable for parenteral administration may comprise one or more fusion proteins of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone, muscle, circulatory system, etc.). In certain embodiments, compositions of the present invention may include a matrix capable of delivering one or more therapeutic compounds (e.g., glycovariant fusion proteins) to a target tissue site (e.g., bone, muscle, circulatory system), providing a structure for the developing tissue and optimally capable of being resorbed into the body. For example, the matrix may provide slow release of a fusion protein of the disclosure. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, fusion proteins can be formulated for oral administration, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (e.g., capsules, tablets, pills, dragees, and powders granules), one or more fusion proteins of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the fusion proteins, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Expression of Glycovariant TNFR2-Fc Fusion Proteins

Applicants constructed vectors for expression of a variety of TNFR2-Fc fusion proteins, each containing an additional N-linked glycosylation site. The control TNFR2-Fc fusion protein (i.e., the basic, or "initial" unmodified form of TNFR2-Fc) has the extracellular domain of human TNFR2 fused to a human IgG1 Fc domain with no intervening linker. The sequence of the initial TNFR2-Fc fusion protein is shown in FIG. 1 (SEQ ID NO:5), and the encoding nucleic acid (including the leader sequence) is shown in FIG. 5 (SEQ ID NO:8). The fusion protein shown in FIG. 1 is more fully designated TNFR2-h(1)Fc. A variant designated TNFR2-h(2)Fc possesses an alternative linker/boundary sequence as shown in FIG. 9 (SEQ ID NO:16) and is encoded by the nucleotide sequence indicated in FIG. 10 (SEQ ID NO: 17). Protein constructs were cloned into a pAID4 vector for expression in mammalian cells (Pearsall et al. PNAS105 (2008): 7082-7087).

For initial experiments, glycovariants of TNFR2-Fc were transiently expressed in HEK293 cells. In brief, in a 500 ml spinner, HEK293T cells were set up at 6×10^5 cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Variants were purified using a variety of techniques, including, for example, protein A column (Mab Select™, GE Healthcare LifeSciences, USA) and eluted with low pH (3.0) glycine buffer, followed by size exclusion chromatography. Proteins were dialyzed against phosphate buffered saline or Tris buffered saline.

While the protein sequences provided in FIG. 5 indicate an N-terminal sequence of "LPA . . . ", a significant portion of each protein showed that the N-terminal leucine had been removed, yielding an N-terminal sequence of "PAQ . . . ". Thus any of the TNFR2-Fc molecules disclosed herein may have one or two amino acids removed from the N-terminus.

Three different leader sequences were considered for use:

(i)    Honey bee mellitin (HBML):
                                   (SEQ ID NO: 10)
       MKFLVNVALVFMVVYISYIYA, (ii)   Tissue Plasminogen Activator (TPA):
                                   (SEQ ID NO: 11)
       MDAMKRGLCCVLLLCGAVFVSP, and (iii)  Native TNFR:
                                   (SEQ ID NO: 15)
       MAPVAVWAALAVGLELWAAAHA.

Additional purification could be achieved by a series of column chromatography steps, including, for example, three or more of the following, in any order: Q sepharose chromatography, phenylsepharose chromatography, hydroxyapatite chromatography, and cation exchange chromatography. The purification could be completed with viral filtration and buffer exchange.

Example 2

Design of Glycovariant TNFR2-Fc Fusion Proteins

Positions for introduction of additional N-linked glycosylation sites were selected by inspection of the co-crystal structure of the extracellular domain of TNFR2 and its ligand TNF (crystal coordinates publicly available), and by application of the principles described herein. The alterations were chosen as being at positions predicted to preserve the TNF antagonist activity of the protein while conferring an extended half-life, and are shown in FIG. 7. Note that the numbering of amino acids is based on the native, unprocessed TNFR2 amino acid sequence, as shown in FIG. 7. The altered TNFR2-Fc fusion proteins were designed to have an additional N-linked sugar moiety at one of the following positions: 47, 48, 62, 114, 155, 202, 203, 222 and 253. Note that the native TNFR2-Fc has N-linked sugar moieties at positions 171 and 193, meaning that the heterolgous domain of the initial TNFR2-Fc fusion protein has a ratio of N-linked sugar moieties to amino acids of 1:117.5. The predicted positions of additional sugar moieties were mapped onto the TNFR2-TNF co-crystal structure and these are shown in FIG. 6. FIG. 8 indicates the predicted location of beta strand secondary structure in the TNFR2 extracellular domain as inferred by sequence comparison and structural homology with related proteins. Each of the new N-linked sites were positioned internal to structural elements. For example, the sites introduced at positions 47 and 48 are internal to the first beta-sheet structural element. After generating and testing proteins with single additional N-linked glycosylation sites, combination mutants were generated and tested.

Example 3

Testing of TNFR2-Fc Glycovariant Proteins

Glycovariants of TNFR2-h(1)Fc were tested in a series of assays to assess functionality of the modified molecules and effects of the modification on pharmacokinetic properties of the molecules.

To assess ligand binding in a cell-free biochemical assay, a Biacore® 3000 biosensor instrument was used. In brief, TNFR2-h(1)Fc variants were loaded into the flow cell and then exposed to TNF. By evaluating kinetic parameters ($k_a$ and $k_d$), a dissociation constant ($K_D$) was calculated.

To assess ligand inhibition, a cell-based assay for TNF signaling was used, essentially as described in Khabar et al. Immunol. Lett. 46 (1995): 107-110. In brief, WEHI cells (ATCC) were cultured in the presence of TNF-alpha (R&D Systems, Minneapolis, Minn.) and Actinomycin D. TNF-alpha causes apoptosis in these cells, and lysis rate detected at $A_{490nm}$. The presence of a TNF-alpha antagonist causes a decrease in the signal which permits the detection of an IC50.

To assess pharmacokinetic properties of the molecules studies were conducted in Sprague-Dawley rats using standard techniques. In brief, after an acclimation period, animals were dosed with a TNFR2-h(1)Fc molecule and bled by tail-nick at hour 6, 10, 24, 32, 48, 72, 96, 144, 216 and 312 after initial dose. The presence of TNFR2-Fc molecules was detected by an ELISA for the human Fc portion.

The data were normalized against data obtained from a native TNFR2-h(1)Fc molecule to minimize variability from experiment to experiment. Normalized values are shown below. Proteins exhibiting desirable qualities are shown in gray and underlined.

| Protein Construct | $K_D$ (TNF-alpha) | IC50 (WEHI Assay) | $T_{1/2}$(Rat) |
|---|---|---|---|
| TNFR-h(1)Fc wt (valued normalized) | 1.0 | 1.0 | 1.0 |
| D47N | 1.6 | 1.9 | Nd* |
| Q48N A50S | _1.7_ | _1.6_ | _1.5_ |
| H62N K64T | No affinity | Nd** | Nd** |
| Q114N R116S | No affinity | Nd** | Nd** |
| E155N | _1.6_ | _1.3_ | _1.6_ |
| S202N | _0.36_ | _0.78_ | _1.3_ |
| T203N P205S | 0.33 | 0.29 | 0.44 |
| T222N | 0.78 | 0.25 | 0.45 |
| G253N | _0.41_ | _1.1_ | _1.3_ |
| D47N E155N | 2.6 | 1.6 | 1.1 |
| D47N S202N | 4.4 | 1.1 | 1.1 |
| D47N G253N | 55 | 3.0 | 1.4 |
| E155N G253N | 3.6 | 0.57 | 0.72 |
| S202N G253N | 1.05 | 0.23 | 0.65 |
| E155N S202N G253N | 1.0 | 0.25 | 0.89 |

*D47N protein was not expressed in sufficient quantity to permit testing in vivo.
**The mutations placing the N-linked sugar at positions 62 or 114 caused complete disruption of ligand binding, and no other properties were evaluated.

The data presented above indicate that nearly half of the variants containing a single additional N-linked site (4 of 9) exhibited substantially improved serum half life while retaining ligand binding and antagonism similar to that of the wild-type molecule. Because of the effects of allometric scaling on serum half-life, changes in serum half-life of 20-30% in rats should provide a meaningful improvement in the dosing regimen for human patients. Interestingly, combination mutations generally seemed to either decrease serum half-life or protein activity, suggesting that, in this molecule, further increases in the density of glycosylation was no longer helpful.

These data demonstrate that, using the teachings provided herein, one can efficiently generate Fc fusion molecules with extended serum half-lives.

Example 4

Pharmacokinetic Rat Assay

Pharmacokinetic properties of the glycovariant molecules may be determined in Sprague-Dawley rats using standard techniques. In brief, after an acclimation period, eight (8) animals are dosed subcutaneously (SC) with a glycovariant molecule and bled by tail-nick at hour 6, 10, 24, 32, 48, 72, 96, 144, 216 and 312 after initial dose. The presence of the glycovariant molecules may be detected using any method suitable for the target protein. For example, the glycovariant Fc fusion protein may be detected using an ELISA for the human Fc portion. The serum elimination half-life ($T_{1/2}$) is calculated for each individual animal. Mean $T_{1/2}$ and standard deviations are calculated for the glycovariant molecule. If not already determined, similar studies may be carried out to determine the mean $T_{1/2}$ and standard deviations for an appropriate control molecule administered at the same dose, such as an Fc fusion protein that does not contain the introduced N-linked glycosylation site. Mean $T_{1/2}$ is analyzed using an appropriate statistical test such as a Student's t-test. The mean $T_{1/2}$ of the glycovariant molecule may be compared to the mean $T_{1/2}$ of an appropriate control molecule.

A study was conducted according to the foregoing methods to compare pharmacokinetic properties of TNFR2-h(1)Fc, Q48N/A50S TNFR2-h(1)Fc, and Q48N/A50S TNFR2-h(2) Fc in rats. This study determined protein concentrations up to 28 days after subcutaneous administration of single doses of 5 mg/kg (n=3 rats per construct).

| Protein Construct | $T_{1/2}$ |
|---|---|
| TNFR2-h(1)Fc (value normalized) | 1.0 |
| Q48N/A50S TNFR2-h(1)Fc | 1.5 |
| Q48N/A50S TNFR2-h(2)Fc | 1.8 |

Compared to TNFR2-h(1)Fc, serum half-lives of the glycovariants Q48N/A50S TNFR2-h(1)Fc and Q48N/A50S TNFR2-h(2)Fc were found to be longer by 50% and 80%, respectively. Remarkably, the maximum serum concentration (Cmax) for Q48N/A50S TNFR2-h(2)Fc was nearly five-fold higher (20.8 vg/ml versus 4.4 vg/ml, p<0.05) than for Q48N/A50S TNFR2-h(1)Fc. These results demonstrate that modification of the linker/boundary region (compare SEQ ID NO: 16 with SEQ ID NO: 5) of a TNFR2-Fc glycovariant can endow that variant (Q48N/A50S TNFR2-h(2)Fc in this example) with improved pharmacokinetic properties. Thus, the linker-hFc sequence provided as SEQ ID NO:18 may be particularly useful in combination with any of the glycovariants disclosed herein.

Example 5

Pharmacokinetic Monkey Assay

Pharmacokinetic properties of the glycovariant molecules may be conducted in cynomolgus monkey model using standard techniques. In brief, 4 male and 4 female cynomolgus monkeys are selected. The animals are experimentally naive at the outset of the procedures, are approximately 2 to 6 years of age, and are at least 2.5 kg in weight. Animals are fed a standard diet and housed according to standard procedures throughout treatment. Animals are dosed with a glycovariant molecule via subcutaneous (SC) or intravenous (IV) administration. Blood samples are collected via femoral venipuncture over a 22 day period at the following timepoints post dosing: 5 minutes, 15 minutes, 30 minutes, 1 hour, 2 hours, 4 hours, 8 hours, 12 hours, 24 hours, 34 hours, 48 hours, 58 hours, 72 hours, 120 hours, 168 hours, 240 hours, 336 hours, 408 hours, and 504 hours. A predose blood sample is also collected. Following blood collection, the samples are stored on ice and the serum isolated by centrifugation. The presence of the glycovariant molecules in the serum samples may be detected using any method suitable for the target protein. For example, the glycovariant Fc fusion protein may be detected using an ELISA for the human Fc portion. The serum elimination half-life ($T_{1/2}$) is calculated for each individual animal. Mean $T_{1/2}$ and standard deviations are calculated for the glycovariant molecule. If not already determined, similar studies may be carried out to determine the mean $T_{1/2}$ and standard deviations for an appropriate control molecule administered at the same dose, such as an Fc fusion protein that does not contain the introduced N-linked glycosylation site. Mean $T_{1/2}$ is analyzed using an appropriate statistical test such as a Student's t-test. The mean $T_{1/2}$ of the glycovariant molecule may be compared to the mean $T_{1/2}$ of an appropriate control molecule.

Example 6

Effect of Q48N/A50S TNFR2-h(1)Fc in a Rat Collagen-Induced-Arthritis Model

The glycovariant Q48N/A50S TNFR2-h(1)Fc was evaluated for efficacy against collagen-induced arthritis in the rat. Bovine collagen type II (Elastin Products, catalog no. CN276) was dissolved in 0.01 M acetic acid and Freund's incomplete adjuvant (Difco, catalog no. 263910) to a concentration of 1 mg/ml and was administered to female Lewis rats (150-200 g) by intradermal injection (2 mg/kg) at the base of the tail on study days 0 and 7. Starting on day 6, rats were treated subcutaneously three times per week with Q48N/A50S TNFR2-h(1)Fc at 3 mg/kg, TNFR2-h(1)Fc at 3 mg/kg, or vehicle. Paw volume was determined by plethysmometry at baseline and multiple time points throughout the study, whereas bone quality was assessed by micro-computed tomography (micro-CT) at study conclusion (ex vivo).

Figure 11:
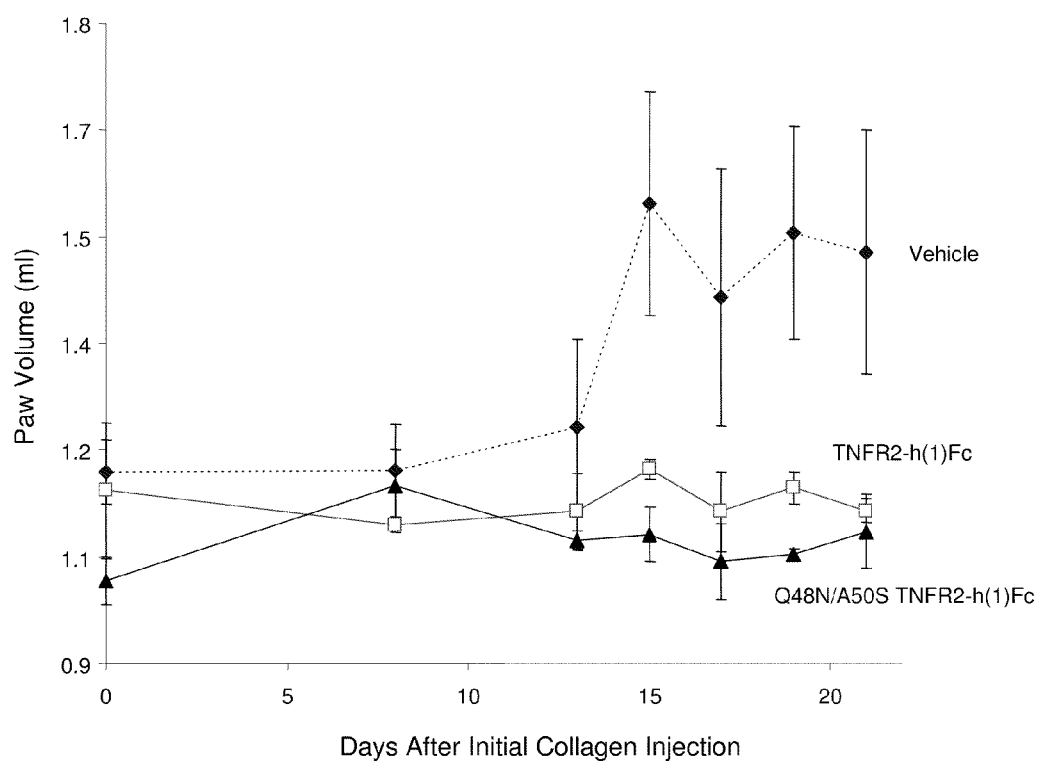
FIG. 11 shows the effect of glycovariant Q48N/A50S TNFR2-h(1)Fc on paw volume as a marker of inflammation in a rat collagen-induced-arthritis model. Collagen was administered on Days 0 and 7, whereas treatment with test articles began on Day 6. Data shown are means±SEM Like TNFR2-h(1)Fc, treatment with Q48N/A50S TNFR2-h(1)Fc prevented the paw swelling observed in vehicle-treated rats during the second half of the study.
Figure 12:
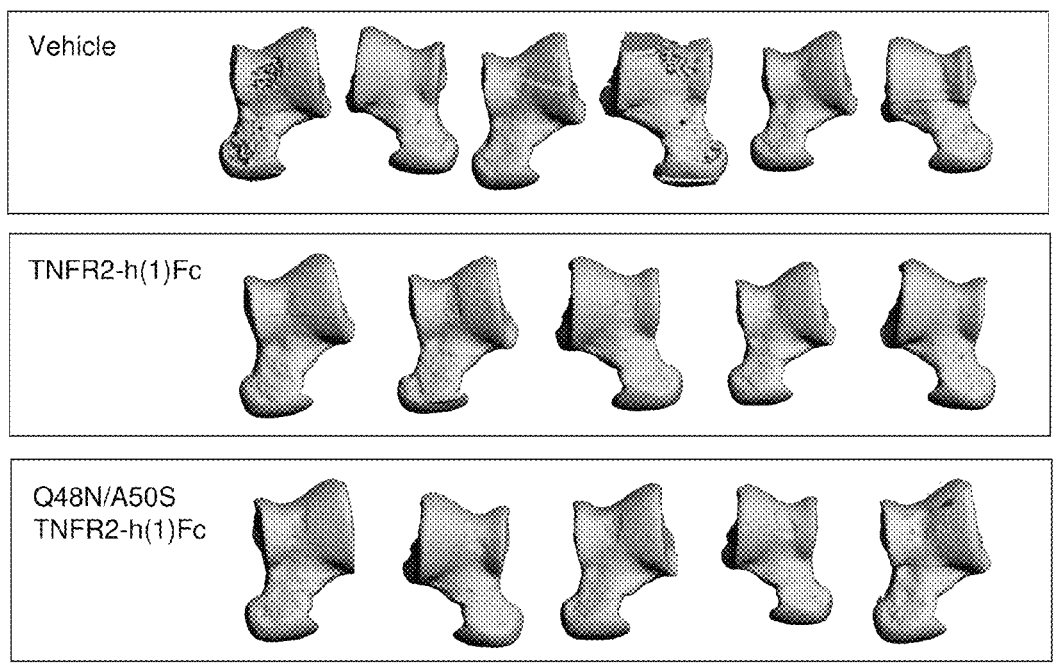
FIG. 12 shows the effect of glycovariant Q48N/A50S TNFR2-h(1)Fc on bone quality in a rat collagen-induced-arthritis model. Tarsal images were obtained ex vivo by micro-computed tomography (micro-CT) after study completion on Day 21. Like TNFR2-h(1)Fc, treatment with Q48N/A50S TNFR2-h(1)Fc prevented the bone erosion observed in vehicle-treated rats.

Paw swelling was used as a marker for collagen-induced inflammation. As expected, paw volume in vehicle-treated rats increased midway through the study and remained elevated until the end. This paw swelling was inhibited as effectively in rats treated with the glycovariant Q48N/A50S TNFR2-h(1)Fc as it was in those treated with the positive control, TNFR2-h(1)Fc (FIG. 11). Moreover, bone quality as assessed by micro-CT was improved similarly in both these treatment groups compared with vehicle-treated controls (FIG. 12), providing additional evidence of anti-inflammatory efficacy. These data demonstrate that the glycovariant Q48N/A50S TNFR2-h(1)Fc has anti-inflammatory efficacy in vivo equivalent to that of its unsubstituted counterpart, TNFR2-h(1)Fc.

Taken together, the foregoing results indicate that certain glycovariants of TNFR2-h(1)Fc, for example Q48N/A50S TNFR2-h(1)Fc, possess increased serum half-life and undiminished anti-inflammatory efficacy compared to TNFR2-h(1)Fc itself.

Incorporation By Reference

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A fusion protein comprising an immunoglobulin Fc domain and at least one heterologous polypeptide domain comprising an amino acid sequence at least 90% identical to SEQ ID NO: 2, wherein at least one of amino acid residues corresponding to D25, E133, and G231 of SEQ ID NO: 2 is replaced by another amino acid residue to create a non-endogenous N-linked glycosylation site.

2. The fusion protein of claim 1, wherein amino acid residue corresponding to D25 of SEQ ID NO: 2 is replaced by an N, and amino acid residue corresponding to E133 of SEQ ID NO: 2 is replaced by an N.

3. The fusion protein of claim 1, wherein amino acid residue corresponding to D25 of SEQ ID NO: 2 is replaced by an N, and amino acid residue corresponding to G231 of SEQ ID NO: 2 is replaced by an N.

4. The fusion protein of claim 1, wherein the heterologous polypeptide domain comprises an amino acid sequence that is at least 95% identical to the amino acid sequence of SEQ ID NO: 2.

5. The fusion protein of claim 4, wherein the heterologous polypeptide domain comprises an amino acid sequence that is at least 99% identical to the amino acid sequence of SEQ ID NO: 2.

6. The fusion protein of claim 1, wherein the fusion protein comprises a heterologous domain selected from:

a) a polypeptide comprising amino acids 13-257 of SEQ ID NO: 7; and b) a polypeptide comprising amino acids 13-257 of SEQ ID NO: 8.

7. The fusion protein of claim 1, wherein the fusion protein comprises a linker fused to the Fc portion, and wherein the linker and Fc portion combined comprises the amino acid sequence of SEQ ID NO: 18.

8. A pharmaceutical preparation comprising the fusion protein of claim 1 and a pharmaceutically acceptable carrier, wherein the preparation is substantially free of pyrogenic materials so as to be suitable for administration to a mammal.

9. The fusion protein of claim 1, wherein amino acid residue corresponding to D25 of SEQ ID NO: 2 is replaced by an N.

10. The fusion protein of claim 1, wherein amino acid residue corresponding to E133 of SEQ ID NO: 2 is replaced by an N.

11. The fusion protein of claim 1, wherein amino acid residue corresponding to G231of SEQ ID NO: 2 is replaced by an N.

12. The fusion protein of claim 2, wherein the fusion protein comprises a linker fused to the Fc portion, and wherein the linker and Fc portion combined comprises the amino acid sequence of SEQ ID NO: 18.

13. The fusion protein of claim 3, wherein the fusion protein comprises a linker fused to the Fc portion, and wherein the linker and Fc portion combined comprises the amino acid sequence of SEQ ID NO: 18.

14. The fusion protein of claim 9, wherein the fusion protein comprises a linker fused to the Fc portion, and wherein the linker and Fc portion combined comprises the amino acid sequence of SEQ ID NO: 18.

15. The fusion protein of claim 10, wherein the fusion protein comprises a linker fused to the Fc portion, and wherein the linker and Fc portion combined comprises the amino acid sequence of SEQ ID NO: 18.

16. The fusion protein of claim 11, wherein the fusion protein comprises a linker fused to the Fc portion, and wherein the linker and Fc portion combined comprises the amino acid sequence of SEQ ID NO: 18.

17. A fusion protein comprising an immunoglobulin Fc domain and at least one heterologous polypeptide domain comprising an amino acid sequence at least 90% identical to SEQ ID NO: 2, wherein amino acid residues corresponding to Q26 and A28 of SEQ ID NO: 2 are each replaced by another amino acid residue to create a non-endogenous N-linked glycosylation site.

18. The fusion protein of claim 17, wherein amino acid residue corresponding to Q25 of SEQ ID NO: 2 is replaced by an N, and amino acid residue corresponding to A28 of SEQ ID NO: 2 is replaced by an S.

19. The fusion protein of claim 17, wherein the heterologous polypeptide domain comprises an amino acid sequence that is at least 95% identical to the amino acid sequence of SEQ ID NO: 2.

20. The fusion protein of claim 19, wherein the heterologous polypeptide domain comprises an amino acid sequence that is at least 99% identical to the amino acid sequence of SEQ ID NO: 2.

21. The fusion protein of claim 17, wherein the fusion protein comprises a polypeptide comprising amino acids 13-257 of SEQ ID NO: 6.

22. The fusion protein of claim 17, wherein the fusion protein comprises a linker fused to the Fc portion, and wherein the linker and Fc portion combined comprises the amino acid sequence of SEQ ID NO: 18.

23. The fusion protein of claim 18, wherein the fusion protein comprises a linker fused to the Fc portion, and wherein the linker and Fc portion combined comprises the amino acid sequence of SEQ ID NO: 18.

24. A pharmaceutical preparation comprising the fusion protein of claim 17 and a pharmaceutically acceptable carrier, wherein the preparation is substantially free of pyrogenic materials so as to be suitable for administration to a mammal.

* * * * *

SEQUENCE LISTING

```
<160> NUMBER OF SEQ ID NOS: 43

<210> SEQ ID NO 1
<211> LENGTH: 489
<212> TYPE: PRT
<213> ORGANISM: Homo sapiens

<400> SEQUENCE: 1

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140
```

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Glu Pro Lys Ser Cys Asp Lys Thr His Thr Cys Pro Pro Cys Pro
                260                 265                 270

Ala Pro Glu Leu Leu Gly Gly Pro Ser Val Phe Leu Phe Pro Pro Lys
            275                 280                 285

Pro Lys Asp Thr Leu Met Ile Ser Arg Thr Pro Glu Val Thr Cys Val
290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
370                 375                 380

Pro Arg Glu Pro Gln Val Tyr Thr Leu Pro Pro Ser Arg Glu Glu Met
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 2
<211> LENGTH: 235
<212> TYPE: PRT
<213> ORGANISM: Homo sapiens

<400> SEQUENCE: 2

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
         35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
             100                 105                 110

Arg Leu Cys Ala Pro Leu Arg Lys Cys Arg Pro Gly Phe Gly Val Ala
         115                 120                 125

Arg Pro Gly Thr Glu Thr Ser Asp Val Val Cys Lys Pro Cys Ala Pro
 130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                 165                 170                 175

Val Cys Thr Ser Thr Ser Pro Thr Arg Ser Met Ala Pro Gly Ala Val
             180                 185                 190

His Leu Pro Gln Pro Val Ser Thr Arg Ser Gln His Thr Gln Pro Thr
         195                 200                 205

Pro Glu Pro Ser Thr Ala Pro Ser Thr Ser Phe Leu Leu Pro Met Gly
 210                 215                 220

Pro Ser Pro Pro Ala Glu Gly Ser Thr Gly Asp
225                 230                 235

<210> SEQ ID NO 3
<211> LENGTH: 1386
<212> TYPE: DNA
<213> ORGANISM: Homo sapiens

<400> SEQUENCE: 3
atggcgcccg tcgccgtctg ggccgcgctg gccgtcggac tggagctctg ggctgcggcg      60
cacgccttgc ccgcccaggt ggcatttaca ccctacgccc ggagcccgg gagcacatgc      120 cggctcagag aatactatga ccagacagct cagatgtgct gcagcaaatg ctcgccgggc     180
caacatgcaa aagtcttctg taccaagacc tcggacaccg tgtgtgactc ctgtgaggac     240
agcacataca cccagctctg gaactgggtt cccgagtgct tgagctgtgg ctcccgctgt     300
agctctgacc aggtggaaac tcaagcctgc actcgggaac agaaccgcat ctgcacctgc     360
aggcccggct ggtactgcgc gctgagcaag caggaggggt gccggctgtg cgcgccgctg     420
cgcaagtgcc gcccgggctt cggcgtggcc agaccaggaa ctgaaacatc agacgtggtg     480
tgcaagccct gtgcccccgg gacgttctcc aacacgactt catccacgga tatttgcagg     540
ccccaccaga tctgtaacgt ggtggccatc cctgggaatg caagcatgga tgcagtctgc     600
acgtccacgt cccccacccg gagtatggcc caggggcag tacacttacc ccagccagtg      660
tccacacgat cccaacacac gcagccaact ccagaaccca gcactgctcc aagcacctcc     720
ttcctgctcc caatgggccc cagccccccca gctgaaggga gcactggcga cttcgctctt     780
ccagttggac tgattgtggg tgtgacagcc ttggtctac taataatagg agtggtgaac     840
tgtgtcatca tgacccaggt gaaaaagaag cccttgtgcc tgcagagaga agccaaggtg     900
cctcacttgc ctgccgataa ggcccggggt acacagggcc ccgagcagca gcacctgctg     960
atcacagcgc cgagctccag cagcagctcc ctggagagct cggccagtgc gttggacaga    1020

```
agggcgccca ctcggaacca gccacaggca ccaggcgtgg aggccagtgg ggccggggag    1080
gcccgggcca gcaccgggag ctcagattct tcccctggtg gccatgggac ccaggtcaat    1140
gtcacctgca tcgtgaacgt ctgtagcagc tctgaccaca gctcacagtg ctcctcccaa    1200
gccagctcca caatgggaga cacagattcc agccctcgg agtccccgaa ggacgagcag    1260
gtccccttct ccaaggagga atgtgccttt cggtcacagc tggagacgcc agagaccctg    1320
ctggggagca ccgaagagaa gccctgccc cttggagtgc ctgatgctgg gatgaagccc    1380
agttaa                                                              1386

<210> SEQ ID NO 4
<211> LENGTH: 705
<212> TYPE: DNA
<213> ORGANISM: Homo sapiens

<400> SEQUENCE: 4
ttgcccgccc aggtggcatt tacaccctac gccccggagc ccgggagcac atgccggctc      60
agagaatact atgaccagac agctcagatg tgctgcagca aatgctcgcc gggccaacat     120
gcaaaagtct tctgtaccaa gacctcggac accgtgtgtg actcctgtga ggacagcaca     180
tacacccagc tctggaactg ggttcccgag tgcttgagct gtggctcccg ctgtagctct     240
gaccaggtgg aaactcaagc ctgcactcgg aacagaacc gcatctgcac ctgcaggccc     300
ggctggtact gcgcgctgag caagcaggag gggtgccggc tgtgcgcgcc gctgcgcaag     360
tgccgcccgg gcttcggcgt ggccagacca ggaactgaaa catcagacgt ggtgtgcaag     420
ccctgtgccc cggggacgtt ctccaacacg acttcatcca cggatatttg caggccccac     480
cagatctgta acgtggtggc catccctggg aatgcaagca tggatgcagt ctgcacgtcc     540
acgtccccca cccggagtat ggccccaggg gcagtacact taccccagcc agtgtccaca     600
cgatcccaac acacgcagcc aactccagaa cccagcactg ctccaagcac ctccttcctg     660
ctcccaatgg gccccagccc cccagctgaa gggagcactg gcgac                    705

<210> SEQ ID NO 5
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
```

```
            115                 120                 125
Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Val Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 6
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Pro Val Ala Val Trp Ala Ala Leu Ala Val Gly Leu Glu Leu
```

-continued

```
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Asn
            35                  40                  45

Thr Ser Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
        130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
        210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
        290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
        370                 375                 380

Pro Arg Glu Pro Gln Val Tyr Thr Leu Pro Pro Ser Arg Glu Glu Met
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430
```

```
Tyr Lys Thr Thr Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 7
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asn Gln
            35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Asn Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300
```

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
        340                 345                 350

Gln Asp Trp Leu Asn Gly Lys Glu Tyr Lys Cys Lys Val Ser Asn Lys
    355                 360                 365

Ala Leu Pro Ala Pro Ile Glu Lys Thr Ile Ser Lys Ala Lys Gly Gln
370                 375                 380

Pro Arg Glu Pro Gln Val Tyr Thr Leu Pro Pro Ser Arg Glu Glu Met
385                 390                 395                 400

Thr Lys Asn Gln Val Ser Leu Thr Cys Leu Val Lys Gly Phe Tyr Pro
            405                 410                 415

Ser Asp Ile Ala Val Glu Trp Glu Ser Asn Gly Gln Pro Glu Asn Asn
        420                 425                 430

Tyr Lys Thr Thr Pro Pro Val Leu Asp Ser Asp Gly Ser Phe Phe Leu
    435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
            485

<210> SEQ ID NO 8
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asn Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
            85                  90                  95

Gly Ser Arg Cys Ser Ser Asp Gln Val Glu Thr Gln Ala Cys Thr Arg
        100                 105                 110

Glu Gln Asn Arg Ile Cys Thr Cys Arg Pro Gly Trp Tyr Cys Ala Leu
    115                 120                 125

Ser Lys Gln Glu Gly Cys Arg Leu Cys Ala Pro Leu Arg Lys Cys Arg
130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
            165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Asn Ser Thr Gly
                245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
        355                 360                 365

Ala Leu Pro Ala Pro Ile Glu Lys Thr Ile Ser Lys Ala Lys Gly Gln
    370                 375                 380

Pro Arg Glu Pro Gln Val Tyr Thr Leu Pro Pro Ser Arg Glu Glu Met
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 9
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
atggcgcccg tcgccgtctg ggccgcgctg ccgtcggac tggagctctg ggctgcggcg      60
cacgccttgc cgcccaggt ggcatttaca ccctacgccc cggagccgg gagcacatgc     120 cggctcagag aatactatga ccagacagct cagatgtgct gcagcaaatg ctcgccgggc     180
caacatgcaa aagtcttctg taccaagacc tcggacaccg tgtgtgactc ctgtgaggac     240
agcacataca cccagctctg gaactgggtt ccgagtgct tgagctgtgg ctcccgctgt     300

```
agctctgacc aggtggaaac tcaagcctgc actcgggaac agaaccgcat ctgcacctgc    360
aggcccggct ggtactgcgc gctgagcaag caggaggggt gccggctgtg cgcgccgctg    420
cgcaagtgcc gcccgggctt cggcgtggcc agaccaggaa ctgaaacatc agacgtggtg    480
tgcaagccct gtgccccggg gacgttctcc aacacgactt catccacgga tatttgcagg    540
ccccaccaga tctgtaacgt ggtggccatc cctgggaatg caagcatgga tgcagtctgc    600
acgtccacgt cccccacccg gagtatggcc ccaggggcag tacacttacc ccagccagtg    660
tccacacgat cccaacacac gcagccaact ccagaaccca gcactgctcc aagcacctcc    720
ttcctgctcc caatgggccc cagcccccca gctgaaggga gcactggcga cgagcccaaa    780
tcttgtgaca aaactcacac atgcccaccg tgcccagcac ctgaactcct ggggggaccg    840
tcagtcttcc tcttcccccc aaaacccaag gacaccctca tgatctcccg gacccctgag    900
gtcacatgcg tggtggtgga cgtgagccac gaagaccctg aggtcaagtt caactggtac    960
gtggacggcg tggaggtgca taatgccaag acaaagccgc gggaggagca gtacaacagc    1020
acgtaccgtg tggtcagcgt cctcaccgtc ctgcaccagg actggctgaa tggcaaggag    1080
tacaagtgca aggtctccaa caaagccctc ccagccccca tcgagaaaac catctccaaa    1140 gccaagggc agccccgaga accacaggtg tacaccctgc ccccatcccg ggaggagatg     1200
accaagaacc aggtcagcct gacctgcctg gtcaaaggct tctatcccag cgacatcgcc    1260
gtggagtggg agagcaatgg gcagccggag aacaactaca agaccacgcc tcccgtgctg    1320
gactccgacg gctccttctt cctctatagc aagctcaccg tggacaagag caggtggcag    1380
caggggaacg tcttctcatg ctccgtgatg catgaggctc tgcacaacca ctacacgcag    1440
aagagcctct ccctgtcccc gggtaaatga                                     1470
```

<210> SEQ ID NO 10
<211> LENGTH: 21
<212> TYPE: PRT
<213> ORGANISM: Apis sp.

<400> SEQUENCE: 10

Met Lys Phe Leu Val Asn Val Ala Leu Val Phe Met Val Val Tyr Ile
1               5                   10                  15

Ser Tyr Ile Tyr Ala
            20

<210> SEQ ID NO 11
<211> LENGTH: 22
<212> TYPE: PRT
<213> ORGANISM: Unknown
<220> FEATURE:
<223> OTHER INFORMATION: Description of Unknown: Tissue plasminogen
      activator leader peptide

<400> SEQUENCE: 11

Met Asp Ala Met Lys Arg Gly Leu Cys Cys Val Leu Leu Leu Cys Gly
1               5                   10                  15

Ala Val Phe Val Ser Pro
            20

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 12

Thr Gly Gly Gly
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Gly Gly Gly
1

<210> SEQ ID NO 14
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 14

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
```

```
                    195                 200                 205
Ala Leu His Xaa His Tyr Thr Gln Lys Ser Leu Ser Leu Ser Pro Gly
    210                 215                 220

Lys
225

<210> SEQ ID NO 15
<211> LENGTH: 22
<212> TYPE: PRT
<213> ORGANISM: Homo sapiens

<400> SEQUENCE: 15

Met Ala Pro Val Ala Val Trp Ala Ala Leu Ala Val Gly Leu Glu Leu
1               5                   10                  15

Trp Ala Ala His Ala
            20

<210> SEQ ID NO 16
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Pro Val Ala Val Trp Ala Ala Leu Ala Val Gly Leu Glu Leu
1               5                   10                  15

Trp Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255
```

```
Asp Thr Gly Gly Gly Thr His Thr Cys Pro Pro Cys Pro Ala Pro Glu
            260                 265                 270

Leu Leu Gly Gly Pro Ser Val Phe Leu Phe Pro Pro Lys Pro Lys Asp
        275                 280                 285

Thr Leu Met Ile Ser Arg Thr Pro Glu Val Thr Cys Val Val Val Asp
290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Glu Glu Met Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
        435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
465                 470                 475                 480

Ser Leu Ser Pro Gly Lys
                485

<210> SEQ ID NO 17
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
atggcgcccg tcgccgtctg ggccgcgctg gccgtcggac tggagctctg ggctgcggcg        60
cacgccttgc ccgcccaggt ggcatttaca ccctacgccc cggagcccgg agcacatgc       120 cggctcagag aatactatga ccagacagct cagatgtgct gcagcaaatg ctcgccgggc       180
caacatgcaa agtcttctg taccaagacc tcggacaccg tgtgtgactc ctgtgaggac       240
agcacataca cccagctctg aactgggtt cccgagtgct tgagctgtgg ctcccgctgt       300
agctctgacc aggtggaaac tcaagcctgc actcgggaac agaaccgcat ctgcaccctgc     360 aggcccggct ggtactgcgc gctgagcaag caggaggggt gccggctgtg cgcgccgctg      420
cgcaagtgcc gccgggctt cggcgtggcc agaccaggaa ctgaaacatc agacgtggtg       480
tgcaagcccg tgccccggga cgttctcc aacacgactt catccacgga tatttgcagg        540
ccccaccaga tctgtaacgt ggtggccatc cctgggaatg caagcatgga tgcagtctgc      600
acgtccacgt cccccacccg gagtatggcc ccaggggcag tacacttacc ccagccagtg      660
tccacacgat cccaacacac gcagccaact ccagaaccca gcactgctcc aagcacctcc     720
```

-continued

```
ttcctgctcc caatgggccc cagcccccca gctgaaggga gcactggcga caccggtggt    780
ggaactcaca catgcccacc gtgcccagca cctgaactcc tggggggacc gtcagtcttc    840
ctcttccccc caaaacccaa ggacaccctc atgatctccc ggacccctga ggtcacatgc    900
gtggtggtgg acgtgagcca cgaagaccct gaggtcaagt tcaactggta cgtggacggc    960
gtggaggtgc ataatgccaa gacaaagccg cgggaggagc agtacaacag cacgtaccgt   1020
gtggtcagcg tcctcaccgt cctgcaccag gactggctga atggcaagga gtacaagtgc   1080
aaggtctcca acaaagccct cccagccccc atcgagaaaa ccatctccaa agccaaaggg   1140
cagccccgag aaccacaggt gtacaccctg cccccatccc gggaggagat gaccaagaac   1200
caggtcagcc tgacctgcct ggtcaaaggc ttctatccca gcgacatcgc cgtggagtgg   1260
gagagcaatg ggcagccgga gaacaactac aagaccacgc tcccgtgct ggactccgac   1320
ggctccttct tcctctatag caagctcacc gtggacaaga gcaggtggca gcaggggaac   1380
gtcttctcat gctccgtgat gcatgaggct ctgcacaacc actacacgca gaagagcctc   1440
tccctgtctc cgggtaaatg a                                             1461
```

<210> SEQ ID NO 18
<211> LENGTH: 229
<212> TYPE: PRT
<213> ORGANISM: Homo sapiens

<400> SEQUENCE: 18

```
Thr Gly Gly Gly Thr His Thr Cys Pro Pro Cys Pro Ala Pro Glu Leu
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser His Glu Asp Pro Glu Val Lys Phe Asn Trp Tyr Val Asp Gly Val
    50                  55                  60
Glu Val His Asn Ala Lys Thr Lys Pro Arg Glu Glu Gln Tyr Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Ala Leu Pro Ala
            100                 105                 110
Pro Ile Glu Lys Thr Ile Ser Lys Ala Lys Gly Gln Pro Arg Glu Pro
        115                 120                 125
Gln Val Tyr Thr Leu Pro Pro Ser Arg Glu Glu Met Thr Lys Asn Gln
    130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Lys Leu
            180                 185                 190
Thr Val Asp Lys Ser Arg Trp Gln Gln Gly Asn Val Phe Ser Cys Ser
        195                 200                 205
Val Met His Glu Ala Leu His Asn His Tyr Thr Gln Lys Ser Leu Ser
    210                 215                 220
Leu Ser Pro Gly Lys
225
```

-continued

```
<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Thr or Ser

<400> SEQUENCE: 19

Cys Xaa Xaa Gly Gly Xaa Cys
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Asp

<400> SEQUENCE: 20

Asn Ser Thr Xaa Ala
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asn Ile Thr Gln Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 22

Gln Ser Xaa Gln Ser
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 23

Glu Phe Ile Xaa Arg Xaa Lys Val
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys or Arg

<400> SEQUENCE: 24

Gly Gly Ser Cys Xaa
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 25

His His His His His His
1               5

<210> SEQ ID NO 26
<211> LENGTH: 257
<212> TYPE: PRT
<213> ORGANISM: Homo sapiens

<400> SEQUENCE: 26

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140
```

```
Pro Gly Phe Gly Val Ala Arg Pro Thr Glu Thr Ser Asp Val Val
145                 150                 155                 160

Cys Lys Pro Cys Ala Pro Gly Thr Phe Ser Asn Thr Thr Ser Ser Thr
            165                 170                 175

Asp Ile Cys Arg Pro His Gln Ile Cys Asn Val Val Ala Ile Pro Gly
        180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
        210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp

<210> SEQ ID NO 27
<211> LENGTH: 8
<212> TYPE: PRT
<213> ORGANISM: Homo sapiens

<400> SEQUENCE: 27

Tyr Tyr Asp Gln Thr Ala Gln Met
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Tyr Asp Asn Thr Ser Gln Met
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Tyr Asn Gln Thr Ala Gln Met
1               5

<210> SEQ ID NO 30
<211> LENGTH: 7
<212> TYPE: PRT
<213> ORGANISM: Homo sapiens

<400> SEQUENCE: 30

Gly Gln His Ala Lys Val Phe
1               5

<210> SEQ ID NO 31
<211> LENGTH: 7
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 31

Gly Gln Asn Ala Thr Val Phe
1               5

<210> SEQ ID NO 32
<211> LENGTH: 7
<212> TYPE: PRT
<213> ORGANISM: Homo sapiens

<400> SEQUENCE: 32

Arg Glu Gln Asn Arg Ile Cys
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Glu Asn Asn Ser Ile Cys
1               5

<210> SEQ ID NO 34
<211> LENGTH: 7
<212> TYPE: PRT
<213> ORGANISM: Homo sapiens

<400> SEQUENCE: 34

Gly Thr Glu Thr Ser Asp Val
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Thr Asn Thr Ser Asp Val
1               5

<210> SEQ ID NO 36
<211> LENGTH: 8
<212> TYPE: PRT
<213> ORGANISM: Homo sapiens

<400> SEQUENCE: 36

Cys Thr Ser Thr Ser Pro Thr Arg
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Cys Thr Asn Thr Ser Pro Thr Arg
1               5
```

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Cys Thr Ser Asn Ser Ser Thr Arg
1               5
```

<210> SEQ ID NO 39
<211> LENGTH: 7
<212> TYPE: PRT
<213> ORGANISM: Homo sapiens

<400> SEQUENCE: 39

```
Val Ser Thr Arg Ser Gln His
1               5
```

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Val Ser Asn Arg Ser Gln His
1               5
```

<210> SEQ ID NO 41
<211> LENGTH: 7
<212> TYPE: PRT
<213> ORGANISM: Homo sapiens

<400> SEQUENCE: 41

```
Ala Glu Gly Ser Thr Gly Asp
1               5
```

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Ala Glu Asn Ser Thr Gly Asp
1               5
```

<210> SEQ ID NO 43
<211> LENGTH: 235
<212> TYPE: PRT
<213> ORGANISM: Homo sapiens

<400> SEQUENCE: 43

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
                20                  25                  30
```

-continued

```
Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235
```